(12) United States Patent
Nagele

(10) Patent No.: US 11,619,632 B2
(45) Date of Patent: Apr. 4, 2023

(54) EARLY-STAGE ALZHEIMER'S DISEASE AUTOANTIBODY BIOMARKERS, TARGET ANTIGENS AND DIAGNOSTIC USES THEREOF

(71) Applicant: ROWAN UNIVERSITY, Glassboro, NJ (US)

(72) Inventor: Robert G. Nagele, Turnersville, NJ (US)

(73) Assignee: Rowan University, Glassboro, NJ (US)

( * ) Notice: Subject to any disclaimer, the term of this patent is extended or adjusted under 35 U.S.C. 154(b) by 188 days.

(21) Appl. No.: 16/061,534

(22) PCT Filed: Dec. 14, 2016

(86) PCT No.: PCT/US2016/066645
§ 371 (c)(1),
(2) Date: Jun. 12, 2018

(87) PCT Pub. No.: WO2017/106338
PCT Pub. Date: Jun. 22, 2017

(65) Prior Publication Data
US 2020/0340990 A1  Oct. 29, 2020

Related U.S. Application Data

(60) Provisional application No. 62/266,790, filed on Dec. 14, 2015.

(51) Int. Cl.
*G01N 33/564* (2006.01)
*G01N 33/68* (2006.01)

(52) U.S. Cl.
CPC ....... *G01N 33/564* (2013.01); *G01N 33/6896* (2013.01); *G01N 2800/2821* (2013.01)

(58) Field of Classification Search
CPC ............. G01N 33/564; G01N 33/6896; G01N 2800/2821; G01N 33/6854
See application file for complete search history.

(56) References Cited

U.S. PATENT DOCUMENTS

2008/0254482 A1  10/2008  Mattoon et al.
2014/0315736 A1  10/2014  Nagele

FOREIGN PATENT DOCUMENTS

| WO | 1999051741 A2 | 10/1999 |
| WO | 2006138275 A2 | 12/2006 |
| WO | 2011142900 A1 | 11/2011 |
| WO | 2013023144 A2 | 2/2013 |

OTHER PUBLICATIONS

Ajit et al., "Loss of P2Y2 Nucleotide Receptors Enhances Early Pathology in the TgCRND8 Mouse Model of Alzheimer's Disease," Mol. Neurobiol., 2014, vol. 49, pp. 1031-1042.

PCT International Search Report and Written Opinion dated Apr. 24, 2017 for PCT International Application PCT/US2016/066645.

Altmann, et al., "Insect cells as hosts for the expression of recombinant glycoproteins", Glycoconj J, vol. 16, No. 2, Feb. 1999, pp. 109-123.

Breiman, "Random Forests", Machine Learning, vol. 45, Issue 1, Oct. 2001, pp. 5-32.

D'Andrea, et al., "Evidence that neurones accumulating amyloid can undergo lysis to form amyloid plaques in Alzheimer's disease", Histopathology, vol. 38, Issue No. 2, Feb. 2001, pp. 120-134.

Demarshall, et al., "Detection of Alzheimer's disease at mild cognitive impairment and disease progression using autoantibodies as blood-based biomarkers", Alzheimer's & Dementia: Diagnosis, Assessment & Disease Monitoring, 3, 2016, pp. 51-62.

He, et al., "In situ synthesis of protein arrays", Curr Opin Biotechnol, vol. 19, Issue 1, Feb. 2008, pp. 4-9.

Kalume, et al., "Molecular mimicry: Cross-reactive antibodies from patients with immune-mediated neurologic disease inhibit neuronal firing", J Neurosci Res, vol. 77, Issue No. 1, Jul. 1, 2004, pp. 82-89.

Manavalan, et al., "Brain site-specific proteome changes in aging-related dementia", Experimental & Molecular Medicine, vol. 45, No. 9, Sep. 1, 2013, pp. e39.

Mangialasche, et al., "Lymphocytic Mitochondrial Aconitase Activity is Reduced in Alzheimer's Disease and Mild Cognitive Impairment", Journal of Alzheimer's Disease, vol. 44, No. 2, Jan. 22, 2015, pp. 649-660.

Mecocci, et al., "Antihistone and anti-dsDNA autoantibodies in Alzheimer's disease and vascular dementia", Biol Psychiatry, vol. 34, Issue No. 6, Sep. 15, 1993, pp. 380-385.

Mecocci, et al., "Serum anti-GFAP and anti-S100 autoantibodies in brain aging, Alzheimer's disease and vascular dementia", J Neuroimmunol, vol. 57, Issues 1-2, Mar. 1995, pp. 165-170.

Nagele, et al., "Intracellular accumulation of β-amyloid1-42 in neurons is facilitated by the α7 nicotinic acetylcholine receptor in Alzheimer's disease", Neuroscience, vol. 110, Issue No. 2, Mar. 12, 2002, pp. 199-211.

Sauer, et al., "Bioenergetics in Glutaryl-Coenzyme A Dehydrogenase Deficiency", J Biol Chem, vol. 280, No. 23, Jun. 10, 2005, pp. 21830-21836.

Stein, et al., "Circulating Autoantibodies Recognize and Bind Dying Neurons Following Injury to the Brain", J Neuropathol Exp Neurol, vol. 61, Issue No. 12, 2002, pp. 1100-1108.

Stoevesandt, et al., "Protein microarrays: high-throughput tools for proteomics", Expert Rev Proteomics, vol. 6, Issue No. 2, Apr. 2009, pp. 145-157.

(Continued)

*Primary Examiner* — Olga N Chernyshev
(74) *Attorney, Agent, or Firm* — Fox Rothschild LLP

(57) ABSTRACT

The present invention provides methods, compositions, and kits for the detection of Early-Stage Alzheimer's disease (AD) autoantibody biomarkers, for the diagnosis of Early-Stage AD, for the identification of a subject at risk for developing Early-Stage AD, and/or for the generation of patient-specific Early-Stage AD autoantibody biomarker profiles.

14 Claims, 10 Drawing Sheets
Specification includes a Sequence Listing.

(56) References Cited

OTHER PUBLICATIONS

Tibshirani, et al., "Diagnosis of multiple cancer types by shrunken centroids of gene expression", Proc Natl Acad Sci USA, vol. 99, No. 10, May 14, 2002, pp. 6567-6572.

Wlls, et al., "Autoantibodies in Autism Spectrum Disorders (ASD)", Ann NY Acad Sci, 1107, 2007, pp. 79-91.

Zabouo et al. CD146 expression is associated with a poor prognosis iin human breast tumors and with enhanced motility in breast cancer cell lines, Breast Cancer Research, Current Medicine Group Ltd., GB, vol. 11, No. 1, Jan. 5, 2009.

Sharma et al., Mimicking the functional hematopoietic stem cell niche in vitro: recapitulation of marrow physiology by hydrogel-based three-dimensional cultures of mesenchymal stromal cells, Haematologica, vol. 97, No. 5, Nov. 4, 2011, pp. 651-660.

Park et al., Glutaric Aciduria Type 1 in Korea: Report of Two Novel Mutations, Journal of Korean Medical Sciences, vol. 25, No. 6, Jan. 1, 2010, p. 957.

Strausberg et al., Generation and initial analysis of more then 15,000 full-length human and mouse cDNA sequences, Proceedings of the National Academy of Science, vol. 99, No. 26, Dec. 24, 2002, pp. 16899-16903.

Extended European Search Report for European Application No. 21198186.5, filed Sep. 22, 2021 dated Feb. 28, 2022.

| Group | n | Age (Years) | (Range) | Sex (% Male) | Ethnicity (% Caucasian) | MMSE |
|---|---|---|---|---|---|---|
| Mild Cognitive Impairment | 50 | 73.0 ± 7.1 | 55-91 | 58 | 94 | 27.9 |
| Controls | 50 | 70.9 ± 5.1 | 62-87 | 56 | 78 | - |
| Mild-Moderate Alzheimer's disease | 50 | 78.5 ± 8.8 | 61-97 | 42 | 88 | 16.5 |
| Mild-Moderate Parkinson's disease | 25 | 73.9 ± 9.5 | 53-88 | 48 | 45 | - |
| Early-Stage Parkinson's disease | 25 | 72.4 ± 2.9 | 67-79 | 56 | 96 | - |
| Multiple Sclerosis | 25 | 53.8 ± 6.6 | 43-67 | 40 | 100 | - |
| Breast Cancer | 11 | 52.5 ± 0.9 | 51-54 | 0 | 100 | - |

Note: MMSE = MiniMental Status Exam

FIG. 1A

| Group | n | CSF Aβ42 | CSF pTau | CSF Aβ42/Tau | CSF AV-45 (whole cerebrum) |
|---|---|---|---|---|---|
| Mild Cognitive Impairment | 50 | 160.6 ± 30.3 | 34.6 ± 16.7 | 2.1 ± 1.3 | 1.4 ± 0.2 |
| EMCI | 32 | 164.8 ± 31.1 | 32.9 ± 15.2 | 2.2 ± 1.4 | 1.4 ± 0.2 |
| LMCI | 18 | 153.1 ± 28.2 | 37.6 ± 19.3 | 1.9 ± 1.2 | 1.3 ± 0.2 |

Note: CSF = cerebrospinal fluid; pTau = phosphorylated tau protein; Aβ42 = amyloid beta 1-42 peptide; AV-45 = fluorescent marker of brain amyloid deposition

FIG. 1B

| MCI vs. Controls | CSF Aβ42 | CSF pTau | CSF Aβ42/Tau | CSF AV-45 (whole cerebrum) |
|---|---|---|---|---|
| Training Error (%) | 4 | 4 | 0 | 2 |
| Testing Error (%) | 0 | 0 | 0 | 0 |

FIG. 1C

Diagnostic Accuracy Table: Autoantibody Biomarker-Target Antigen Interaction for All 50 Target Antigens of Table 1

| MCI (n = 25) vs. | | | | | | MCI (n = 11) vs. |
|---|---|---|---|---|---|---|
| | Age Matched Controls | Mild-Moderate AD | Early-Stage PD | Mild-Moderate PD | Multiple Sclerosis | Breast Cancer |
| n | 25 | *50 | 25 | 25 | 25 | 11 |
| Sensitivity % | 100.0 | 100.0 | 100.0 | 96.0 | 100.0 | 100.0 |
| Specificity % | 100.0 | 98.0 | 96.0 | 96.0 | 100.0 | 100.0 |
| PPV % | 100.0 | 96.2 | 96.2 | 96.0 | 100.0 | 100.0 |
| NPV % | 100.0 | 100.0 | 100.0 | 96.0 | 100.0 | 100.0 |
| Overall Accuracy % | 100.0 | 98.7 | 98.0 | 96.0 | 100.0 | 100.0 |
| Overall Error % | 0 | 1.3 | 2.0 | 4.0 | 0 | 0 |

FIG. 2A

Diagnostic Accuracy Table: Autoantibody Biomarker-Target Antigen Interaction for Top 25 of 50 Target Antigens of Table 1

| MCI (n = 25) vs. | | | | | | MCI (n = 11) vs. |
|---|---|---|---|---|---|---|
| | Age Matched Controls | Mild-Moderate AD | Early-Stage PD | Mild-Moderate PD | Multiple Sclerosis | Breast Cancer |
| | 25 | *50 | 25 | 25 | 25 | 11 |
| Sensitivity % | 100.0 | 100.0 | 100.0 | 100.0 | 100.0 | 100.0 |
| Specificity % | 100.0 | 98.0 | 96.0 | 96.0 | 100.0 | 100.0 |
| PPV % | 100.0 | 96.2 | 96.2 | 96.2 | 100.0 | 100.0 |
| NPV % | 100.0 | 100.0 | 100.0 | 100.0 | 100.0 | 100.0 |
| Overall Accuracy % | 100.0 | 98.7 | 98.0 | 98.0 | 100.0 | 100.0 |
| Overall Error % | 0 | 1.3 | 2.0 | 2.0 | 0 | 0 |

FIG. 2B

Diagnostic Accuracy Table: Autoantibody Biomarker-Target Antigen Interaction for Bottom 25 of 50 Target Antigens of Table 1

| MCI (n = 25) vs. | Age Matched Controls | Mild-Moderate AD | Early-Stage PD | Mild-Moderate PD | Multiple Sclerosis | MCI (n = 11) vs. Breast Cancer |
|---|---|---|---|---|---|---|
| n | 25 | *50 | 25 | 25 | 25 | 11 |
| Sensitivity % | 100.0 | 100.0 | 100.0 | 100.0 | 96.0 | 100.0 |
| Specificity % | 96.0 | 94.0 | 92.0 | 96.0 | 92.0 | 81.8 |
| PPV % | 96.2 | 89.3 | 92.6 | 96.2 | 92.3 | 84.6 |
| NPV % | 100.0 | 100.0 | 100.0 | 100.0 | 95.8 | 100.0 |
| Overall Accuracy % | 98.0 | 96.0 | 96.0 | 98.0 | 94.0 | 90.9 |
| Overall Error % | 2.0 | 4.0 | 4.0 | 2.0 | 6.0 | 9.1 |

FIG. 2C

Diagnostic Accuracy Table: Autoantibody Biomarker-Target Antigen Interaction for Top 10 of 50 Target Antigens of Table 1

| MCI (n = 25) vs. | Age Matched Controls | Mild-Moderate AD | Early-Stage PD | Mild-Moderate PD | Multiple Sclerosis | MCI (n = 11) vs. Breast Cancer |
|---|---|---|---|---|---|---|
| n | 25 | *50 | 25 | 25 | 25 | 11 |
| Sensitivity % | 96.0 | 96.0 | 96.0 | 96.0 | 96.0 | 100.0 |
| Specificity % | 100.0 | 96.0 | 100.0 | 96.0 | 100.0 | 100.0 |
| PPV % | 100.0 | 98.0 | 100.0 | 96.0 | 100.0 | 100.0 |
| NPV % | 96.2 | 92.3 | 96.0 | 96.0 | 96.0 | 100.0 |
| Overall Accuracy % | 98.0 | 96.0 | 98.0 | 96.0 | 98.0 | 100.0 |
| Overall Error % | 2.0 | 4.0 | 2.0 | 4.0 | 2.0 | 0 |

FIG. 2D

Low CSF Abeta chart for the 50 MCI (Early-Stage AD) patient samples used in this study EMCI = early MCI LMCI = late MCI ROC curve assessment of diagnostic utility of top 10, top 25 and bottom 25 AD-associated MCI biomarkers

| MCI (n=25) vs. | Top 10, Top 25 and Bottom 25 Values | | | | | | | | |
|---|---|---|---|---|---|---|---|---|---|
| | Top 10 Markers | | | Top 25 Markers | | | Bottom 25 Markers | | |
| | AUC (95% CI) | Sensitivity (95% CI) | Specificity (95% CI) | AUC (95% CI) | Sensitivity (95% CI) | Specificity (95% CI) | AUC (95% CI) | Sensitivity (95% CI) | Specificity (95% CI) |
| Age Matched Controls (n=25) | 1 | 1 | 1 | 1 | 1 | 1 | 1 | 1 | 1 |
| Early-Stage PD (n=25) | 1 | 1 | 1 | 1 | 1 | 1 | 0.9712 (0.9264,1) | 0.92 (0.8,1) | 1 |
| Mild-Moderate PD (n=25) | 0.9984 (0.994,1) | 1 | 0.96 (0.88,1) | 1 | 1 | 1 | 0.9872 (0.961,1) | 0.96 (0.88,1) | 1 |
| Mild-Moderate AD1 (n=25*) | 1 | 1 | 1 | 1 | 1 | 1 | 0.9968 (0.9892, 1) | 1 | 0.96 (0.88,1) |
| Mild-Moderate AD2 (n=25*) | 1 | 1 | 1 | 1 | 1 | 1 | 0.9968 (0.9892, 1) | 1 | 0.96 (0.88,1) |
| Multiple Sclerosis (n=25) | 1 | 1 | 1 | 1 | 1 | 1 | 0.968 (0.9234, 1) | 0.92 (0.8,1) | 0.96 (0.88,1) |
| Breast Cancer (n=11) | 1 | 1 | 1 | 1 | 1 | 1 | 0.9587 (0.8877, 1) | 1 | 0.8182 (0.5455,1) |

FIG. 4

ROC curve assessment of the diagnostic utility of the top 50 AD-associated MCI biomarkers

| | Top 50 Values | Top 50 Markers | |
|---|---|---|---|
| MCI (n=25) vs. | AUC (95% CI) | Sensitivity (95% CI) | Specificity (95% CI) |
| Age-Matched Controls (n=25) | 1 | 1 | 1 |
| Early-Stage PD (n=25) | 1 | 1 | 1 |
| Mild-Moderate PD (n=25) | 1 | 1 | 1 |
| Mild-Moderate AD 1 (n=25*) | 1 | 1 | 1 |
| Mild-Moderate AD 2 (n=25*) | 1 | 1 | 1 |
| Multiple Sclerosis (n=25) | 1 | 1 | 1 |
| Breast Cancer (n=11) | 1 | 1 | 1 |

FIG. 5A

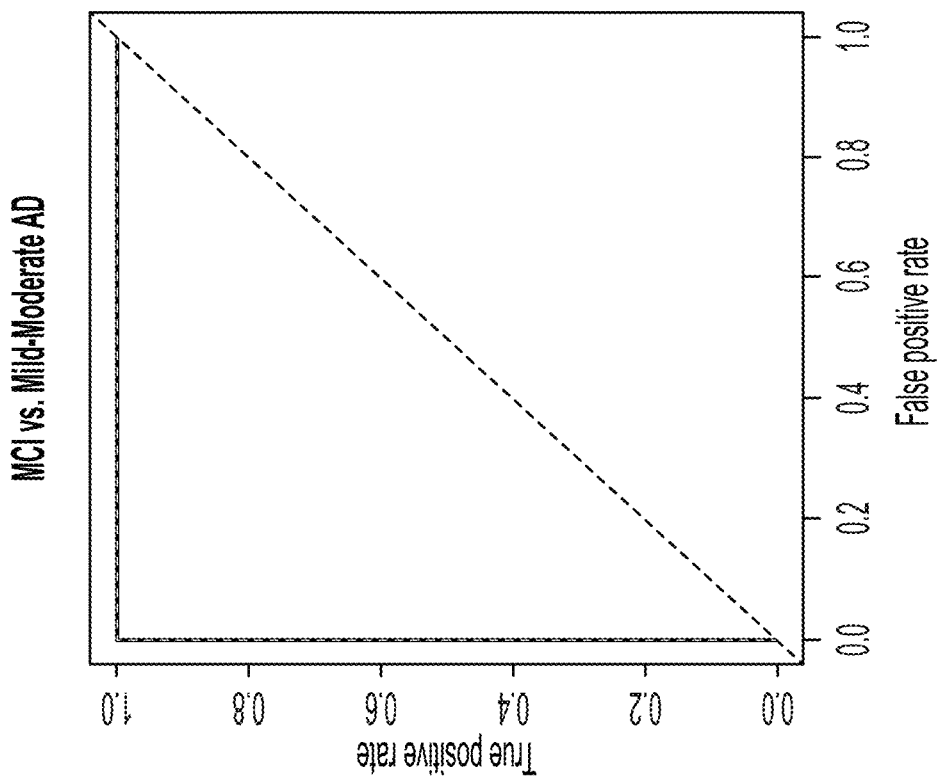
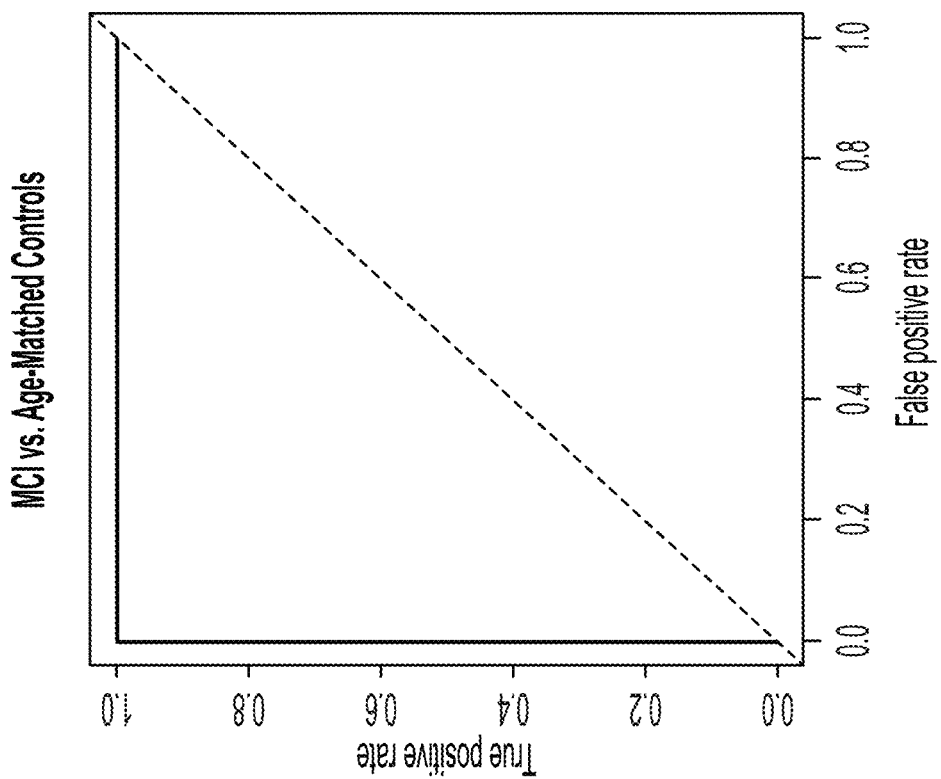
FIG. 5B

EARLY-STAGE ALZHEIMER'S DISEASE AUTOANTIBODY BIOMARKERS, TARGET ANTIGENS AND DIAGNOSTIC USES THEREOF

CROSS-REFERENCE TO RELATED APPLICATION

The present application is a 35 U.S.C. § 371 national phase application of, and claims priority to, International Application No. PCT/US2016/066645, filed Dec. 14, 2016, which claims priority under 35 U.S.C. § 119(e) to U.S. Provisional Application No. 62/266,790, filed Dec. 14, 2015, all of which applications are incorporated herein by reference in their entireties.

BACKGROUND

I. Autoantibodies

An autoantibody is an antibody manufactured by an individual's immune system that is directed against an individual's own proteins acting as antigens. Antibodies are normally produced in response to a foreign protein or substance within the body, typically a pathogen, which is an infectious organism. Normally, the immune system is able to recognize and ignore the body's own cells and not overreact to non-threatening substances in the environment, such as foods. Sometimes, however, the immune system ceases to recognize one or more of the body's normal constituents as "self", leading to production of autoantibodies. These autoantibodies can attack the body's own cells, tissues, and/or organs, causing inflammation and damage.

Serum autoantibodies have been implicated in a wide variety of neurological diseases and syndromes. Neuron-binding autoantibodies have been detected in sera from individuals exhibiting obsessive compulsive disorder, Sydenham's chorea, pediatric autoimmune neuropsychiatric disorders associated with streptococcal infection ("PANDAS"), and Hashimoto's encephalopathy. Schizophrenia has also been linked to the appearance of autoantibodies, including several directed against neuronal surface receptors. Systemic lupus erythematosus ("SLE"), known to be caused by antinuclear antibodies, appears to trigger early cognitive and memory loss components consistent with the presence of a subset of anti-DNA antibodies that cross-react with the N-methyl-D-aspartate receptor ("NMDAR"). Also, brain-reactive antibodies in mothers of autistic children elicit behavioral abnormalities in progeny when administered to pregnant mammals.

Moreover, among neurodegenerative diseases, autoantibodies have been found in Parkinson's disease, Autism spectrum disorders (ASDs), amyotrophic lateral sclerosis, multiple sclerosis, Guillain-Barre syndrome, chronic peripheral neuropathy, optic neuritis, vascular dementia, and AD. In the case of AD, there have been numerous reports of patients having high titers of autoantibodies to both non-brain and brain-associated targets, including neuron-binding autoantibodies. Moreover, several specific autoantibody targets have been identified, including aldolase, heavy neurofilament subunit, histone, tubulin, glial fibrillary acid protein, and S-100.

Specifically, autoimmunity and autoantibodies have been shown to be involved in the pathogenesis of ASDs (Ashwood et al. (2006) J Leukocyte Biol 80, 1-11; Wills et al. (2007) Ann N.Y. Acad Sci 1107, 79-91; Zimmerman et al. (2007) Brain Behav Immun 21, 351-357). The binding of autoantibodies to neurons can disrupt the normal pattern of neurodevelopment at critical stages. Autoantibodies reactive to the brain have been reported in autistic children, and several autoimmune factors including brain-specific autoantibodies, impaired lymphocyte function, abnormal cytokine regulation, and viral associations have been implicated (Singh and Rivas (2004) Neurosci Lett 355, 53-56). For example, Singh and Rivas (2004) have shown that the serum of autistic children contains brain-specific autoantibodies. In a study of 68 autistic children at 4-12 years of age, autoantibodies to the caudate nucleus, cerebral cortex and cerebellum were detected in 49%, 18% and 9%, respectively, of autistic children, but not in normal children. Another study has shown that children with Tourette syndrome possess anti-striatal antibodies, and infusion of these antibodies into the rat striatum caused neuronal dysfunction similar to Tourette syndrome (Hallet et al. (2000) J Neuroimmunol 111, 195-202). Other anti-brain antibodies have also been found in autistic patients, including antibodies to serotonin receptor, myelin basic protein, axon filament protein, cerebellar neurofilaments, nerve growth factor, brain endothelial proteins and antibodies directed against other unidentified brain proteins. ASDs have been linked to specific brain abnormalities. Neurological observations and neuroimaging studies have provided evidence that many brain regions can be affected in autism, including the cerebellum, cerebral cortex, amygdala, hippocampus, basal ganglia and the brain stem (Akshoomoff et al., 2002; Acosta and Pearl (2004) Semin Pediatr Neurol 11, 205-213). Cerebellar abnormalities are also common in ASD, hallmarked by a scarcity of Purkinje and granule cells (Courchesne et al., 2001).

A strong link between the presence of anti-neuronal autoantibodies and neurological disease has been shown in children in cases following streptococcal infections, such as in obsessive compulsive disorder (OCD), Sydenham's chorea, Tourette syndrome, PANDAS, and paraneoplasia, and in elderly patients with SLE that show both cognitive and memory loss (Swedo et al. (1989) Am J Psychiatry 154, 110-2; Kalume et al. (2004) J Neurosci Res 77, 82-89; Tanaka et al. (2004) J Neurological Sci 217, 25-30). DeGeorgio et al. (2001) Nature Med 11, 1189-1193 and Kowal et al. (2004) Immunity 21, 179-188, report that a subset of anti-DNA antibodies in SLE patients cross-reacts with the NMDA (N-methyl-D-aspartate) subtype of glutamate receptors (NR2a and NR2b) by means of molecular mimicry and induces neuronal injury and death both in vivo and in vitro.

II. Alzheimer's Disease

Alzheimer's disease (AD) is a progressive and devastating neurodegenerative disorder of the elderly that is highlighted by a dramatic reduction of memory and cognition and linked to loss of neurons and synapses (Selkoe (2002) Science 298, 789-791). Additional key pathological features include the deposition of amyloid beta (Aβ), especially the 42-amino acid peptide (Aβ42), within neurons, amyloid plaques and in the walls of brain blood vessels, as well as the appearance of neurofibrillary tangles, glial activation and widespread inflammation (Schwab et al. (2008) J Alzheimers Dis 13, 359-369; Thal et al. (2008) Acta Neuropathol 115, 599-609; Weisman et al. (2006) Vitam Horm 74, 505-530). Aβ42 deposition within neurons is initiated early in the course of the disease, precedes amyloid plaque and tangle formation, and temporally and spatially coincides with loss of synapses in human AD and transgenic mouse brains (D'Andrea et al. (2001) Histopathology 38, 120-134; Nagele et al. (2002) Neuroscience 110, 199-211; Gouras et al. (2000) Am J Pathol 156, 15-20).

Studies have reported the presence of immunoglobulin (Ig)-immunopositive neurons in histological sections of post-mortem AD brains, which were only rarely observed in comparable brain regions of non-demented, age-matched controls (Stein et al. (2002) J Neuropathol Exp Neurol 61, 1100-8; Bouras et al. (2005) Brain Res Brain Res Rev 48, 477-87; D'Andrea (2003) Brain Res Brain Res Rev 982, 19-30). The presence of specific brain-reactive autoantibodies in the serum of AD patients has also been reported. (Bouras et al. (2005) Brain Res Brain Res Rev 48, 477-87; Kulmala et al. (1987) Exp Aging Res 13, 67-72; Mecocci et al. (1993) Biol Psychiatry 34, 380-5; Mecocci et al. (1995) J Neuroimmunol 57, 165-70; Weksler et al. (2002) Exp Gerontol 37, 971-979).

SUMMARY OF THE INVENTION

At least one aspect of the present invention provides a method for detecting AD related autoantibody biomarkers in a subject in need of such detection comprising obtaining an immunoglobulin-containing biological sample from the subject, performing an assay to determine the presence or absence of at least one or more autoantibody biomarker in the biological sample, forming immunocomplexes between autoantibodies targeting at least two of said biomarkers, and detecting the presence of said immunocomplexes, wherein such detection identifies patients' risk of developing AD.

In one embodiment, the present invention provides a method for detecting Early-Stage AD autoantibody biomarkers in a subject in need of such detection comprising obtaining an immunoglobulin-containing biological sample from the subject, and performing an assay to determine the presence or absence of at least one Early-Stage AD autoantibody biomarker in the biological sample.

In another embodiment, the present invention provides a method for diagnosing Early-Stage AD in a subject in need of such diagnosis comprising obtaining an immunoglobulin-containing biological sample from the subject, performing an assay to determine the presence or absence of at least one Early-Stage AD autoantibody biomarker in the biological sample, and diagnosing Early-Stage AD if at least one Early-Stage AD autoantibody biomarker is present.

In another embodiment, the present invention provides a method of identifying a subject at risk for developing Early-Stage AD comprising obtaining an immunoglobulin-containing biological sample from the subject, performing an assay to determine the presence or absence of at least one Early-Stage AD autoantibody biomarker in the biological sample, and identifying the subject as at risk for developing Early-Stage AD if at least one Early-Stage AD autoantibody biomarker is present.

In another embodiment, the present invention provides a method of generating a patient-specific Early-Stage AD autoantibody biomarker profile comprising obtaining an immunoglobulin-containing biological sample from a patient, performing an assay to determine the presence or absence of at least one Early-Stage AD autoantibody biomarker in the biological sample, and generating a patient-specific Early-Stage AD autoantibody biomarker profile of the Early-Stage AD autoantibody biomarker(s) present in the sample.

In some embodiments, the assay performed to determine the presence or absence of at least one Early-Stage AD autoantibody biomarker uses at least one (1) target antigen or antigenic fragments thereof.

In some embodiments, the assay performed to determine the presence or absence of at least one Early-Stage AD autoantibody biomarker uses at least five (5) target antigens or antigenic fragments thereof.

In some embodiments, the assay performed to determine the presence or absence of at least one Early-Stage AD autoantibody biomarker uses at least ten (10) target antigens or antigenic fragments thereof.

In some embodiments, the assay performed to determine the presence or absence of at least one Early-Stage AD autoantibody biomarker uses at least twenty-five (25) target antigens or antigenic fragments thereof.

In some embodiments, the assay performed to determine the presence or absence of at least one Early-Stage AD autoantibody biomarker uses at least fifty (50) target antigens or antigenic fragments thereof.

In some embodiments, the assay performed to determine the presence or absence of at least one Early-Stage AD autoantibody biomarker uses between one (1) and five (5) (inclusive) target antigens or antigenic fragments thereof.

In some embodiments, the assay performed to determine the presence or absence of at least one Early-Stage AD autoantibody biomarker uses between one (1) and ten (10) (inclusive) target antigens or antigenic fragments thereof.

In some embodiments, the assay performed to determine the presence or absence of at least one Early-Stage AD autoantibody biomarker uses between five (5) and ten (10) (inclusive) target antigens or antigenic fragments thereof.

In some embodiments, the assay performed to determine the presence or absence of at least one Early-Stage AD autoantibody biomarker uses between one (1) and twenty five (25) (inclusive) target antigens or antigenic fragments thereof.

In some embodiments, the assay performed to determine the presence or absence of at least one Early-Stage AD autoantibody biomarker uses between five (5) and twenty five (25) (inclusive) target antigens or antigenic fragments thereof.

In some embodiments, the assay performed to determine the presence or absence of at least one Early-Stage AD autoantibody biomarker uses between ten (10) and twenty five (25) (inclusive) target antigens or antigenic fragments thereof.

In some embodiments, the assay performed to determine the presence or absence of at least one Early-Stage AD autoantibody biomarker uses between one (1) and fifty (50) (inclusive) target antigens or antigenic fragments thereof.

In some embodiments, the assay performed to determine the presence or absence of at least one Early-Stage AD autoantibody biomarker uses at least one target antigen or antigenic fragments thereof from Table 1.

In some embodiments, the assay performed to determine the presence or absence of at least one Early-Stage AD autoantibody biomarker uses between one (1) and five (5) (inclusive) target antigens from Table 1 or antigenic fragments thereof.

In some embodiments, the assay performed to determine the presence or absence of at least one Early-Stage AD autoantibody biomarker uses between one (1) and ten (10) (inclusive) target antigens from Table 1 or antigenic fragments thereof.

In some embodiments, the assay performed to determine the presence or absence of at least one Early-Stage AD autoantibody biomarker uses between five (5) and ten (10) (inclusive) target antigens from Table 1 or antigenic fragments thereof.

In some embodiments, the assay performed to determine the presence or absence of at least one Early-Stage AD autoantibody biomarker uses between one (1) and twenty five (25) (inclusive) target antigens from Table 1 or antigenic fragments thereof.

In some embodiments, the assay performed to determine the presence or absence of at least one Early-Stage AD autoantibody biomarker uses between ten (10) and twenty five (25) (inclusive) target antigens from Table 1 or antigenic fragments thereof.

In some embodiments, the assay performed to determine the presence or absence of at least one Early-Stage AD autoantibody biomarker uses between five (5) and twenty five (25) (inclusive) target antigens from Table 1 or antigenic fragments thereof.

In some embodiments, the assay performed to determine the presence or absence of at least one Early-Stage AD autoantibody biomarker uses between one (1) and fifty (50) (inclusive) target antigens from Table 1 or antigenic fragments thereof.

In another embodiment, the present invention provides a substrate on which at least one target antigen or antigenic fragment thereof that is specific for at least one Early-Stage AD autoantibody biomarker is immobilized.

In some embodiments, at least five (5) target antigens or antigenic fragments thereof are immobilized on the substrate.

In some embodiments, at least ten (10) target antigens or antigenic fragments thereof are immobilized on the substrate.

In some embodiments, at least twenty-five (25) target antigens or antigenic fragments thereof are immobilized on the substrate.

In some embodiments, at least fifty (50) target antigens or antigenic fragments thereof are immobilized on the substrate.

In some embodiments, between one (1) and five (5) (inclusive) target antigens or antigenic fragments thereof are immobilized on the substrate.

In some embodiments, between one (1) and ten (10) (inclusive) target antigens or antigenic fragments thereof are immobilized on the substrate.

In some embodiments, between five (5) and ten (10) (inclusive) target antigens or antigenic fragments thereof are immobilized on the substrate.

In some embodiments, between five (5) and twenty-five (25) (inclusive) target antigens or antigenic fragments thereof are immobilized on the substrate.

In some embodiments, between ten (10) and twenty-five (25) (inclusive) target antigens or antigenic fragments thereof are immobilized on the substrate.

In some embodiments, between one (1) and twenty-five (25) (inclusive) target antigens or antigenic fragments thereof are immobilized on the substrate.

In some embodiments, between one (1) and fifty (50) (inclusive) target antigens or antigenic fragments thereof are immobilized on the substrate.

In some embodiments, at least one target antigen or antigenic fragments thereof from Table 1 is immobilized on the substrate.

In some embodiments, at least five (5) target antigens from Table 1 or antigenic fragments thereof are immobilized on the substrate.

In some embodiments, at least ten (10) target antigens from Table 1 or antigenic fragments thereof are immobilized on the substrate.

In some embodiments, at least twenty-five (25) target antigens from Table 1 or antigenic fragments thereof are immobilized on the substrate.

In some embodiments, at least fifty (50) target antigens from Table 1 or antigenic fragments thereof are immobilized on the substrate.

In some embodiments, between one (1) and five (5) (inclusive) target antigens from Table 1 or antigenic fragments thereof are immobilized on the substrate.

In some embodiments, between one (1) and ten (10) (inclusive) target antigens from Table 1 or antigenic fragments thereof are immobilized on the substrate.

In some embodiments, between five (5) and ten (10) (inclusive) target antigens from Table 1 or antigenic fragments thereof are immobilized on the substrate.

In some embodiments, between five (5) and twenty-five (25) (inclusive) target antigens from Table 1 or antigenic fragments thereof are immobilized on the substrate.

In some embodiments, between ten (10) and twenty-five (25) (inclusive) target antigens from Table 1 or antigenic fragments thereof are immobilized on the substrate.

In some embodiments, between one (1) and twenty-five (25) (inclusive) target antigens from Table 1 or antigenic fragments thereof are immobilized on the substrate.

In some embodiments, between one (1) and fifty (50) (inclusive) target antigens from Table 1 or antigenic fragments thereof are immobilized on the substrate.

In a further embodiment, the present invention provides a kit or an article of manufacture for detecting Early-Stage AD autoantibody biomarkers.

In some embodiments, the kit contains at least one target antigen or antigenic fragments thereof.

In some embodiments, the kit contains at least five (5) target antigens or antigenic fragments thereof.

In some embodiments, the kit contains at least twenty-five (25) target antigens or antigenic fragments thereof.

In some embodiments, the kit contains at least fifty (50) target antigens or antigenic fragments thereof.

In some embodiments, the kit contains between one (1) and five (5) (inclusive) target antigens or antigenic fragments thereof.

In some embodiments, the kit contains between one (1) and ten (10) (inclusive) target antigens or antigenic fragments thereof.

In some embodiments, the kit contains between one (1) and twenty five (25) (inclusive) target antigens or antigenic fragments thereof.

In some embodiments, the kit contains between five (5) and ten (10) (inclusive) target antigens or antigenic fragments thereof.

In some embodiments, the kit contains between five (5) and twenty-five (25) (inclusive) target antigens or antigenic fragments thereof.

In some embodiments, the kit contains between ten (10) and twenty-five (25) (inclusive) target antigens or antigenic fragments thereof.

In some embodiments, the kit contains between one (1) and twenty-five (25) (inclusive) target antigens or antigenic fragments thereof.

In some embodiments, the kit contains at least one target antigen from Table 1 or antigenic fragments thereof.

In some embodiments, the kit contains at least five (5) target antigens from Table 1 or antigenic fragments thereof.

In some embodiments, the kit contains at least twenty-five (25) target antigens from Table 1 or antigenic fragments thereof.

In some embodiments, the kit contains at least fifty (50) target antigens from Table 1 or antigenic fragments thereof.

In some embodiments, the kit contains between one (1) and five (5) (inclusive) target antigens from Table 1 or antigenic fragments thereof.

In some embodiments, the kit contains between one (1) and ten (10) (inclusive) target antigens from Table 1 or antigenic fragments thereof.

In some embodiments, the kit contains between five (5) and ten (10) (inclusive) target antigens from Table 1 or antigenic fragments thereof.

In some embodiments, the kit contains between five (5) and fifteen (15) (inclusive) target antigens from Table 1 or antigenic fragments thereof.

In some embodiments, the kit contains between five (5) and twenty-five (25) (inclusive) target antigens from Table 1 or antigenic fragments thereof.

In some embodiments, the kit contains between ten (10) and twenty-five (25) (inclusive) target antigens from Table 1 or antigenic fragments thereof.

In some embodiments, the kit contains between one (1) and twenty-five (25) (inclusive) target antigens from Table 1 or antigenic fragments thereof.

BRIEF DESCRIPTION OF THE DRAWINGS

FIGS. 1A, 1B and 1C represent demographic data of participants in Example 1.

FIGS. 2A, 2B, 2C and 2D represent diagnostic accuracy of the autoantibody biomarker-target antigen interactions of Example 1.

FIG. 4. represents the ROC curve assessment of Testing Set subjects of Example 1.

FIGS. 5A and 5B represent the ROC curve assessment of top 50 Early-Stage AD-Associated Target Antigens of Example 1 (Testing Set only).

DETAILED DESCRIPTION OF THE INVENTION

Figure 3:
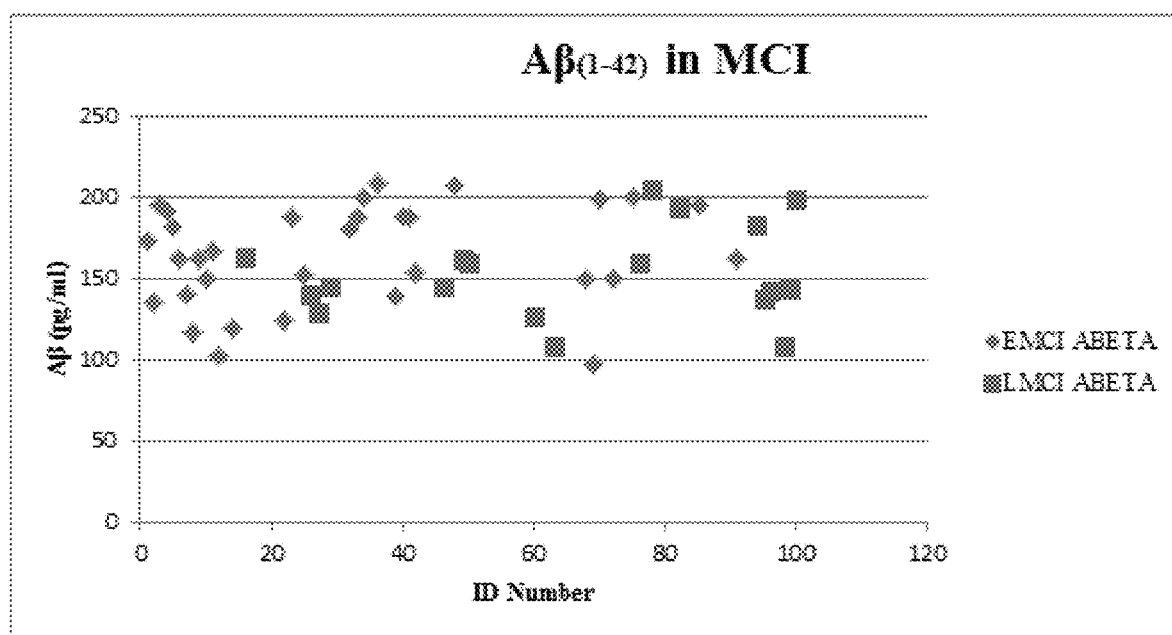
FIG. 3. represents sera CSF Aβ42 levels in participants of Example 1.

It is known that, in roughly 60% of all patients that come to see their doctor for the first time with early memory or cognitive problems (called mild cognitive impairment or MCI), the symptoms are actually caused by early stages of ongoing AD pathology; the remaining 40% are due to other factors such as side-effects of new medications, depression or poor vascular perfusion of the brain. For physicians to properly treat their patients, it is essential for them to know the exact cause of their MCI. The purpose of this invention is to provide a means for physicians to make this distinction and to identify individuals whose MCI is due to an early stage of AD pathology. The pathology of MCI represents a critical area of research, as early detection and diagnosis of AD can lead to a better prognosis. Currently, there is no outstanding cure for AD, but a number of drugs are being tested in the pharma pipeline. A person diagnosed with AD lives for 4 to 8 years on average after diagnosis, thus making early detection of AD of critical importance. Symptoms of MCI often include one or more of the following; trouble remembering names, problems forming words, difficulty in performing tasks in either work or social settings, losing or misplacing objects frequently, trouble planning or organizing, and generally forgetting material, especially material that has been recently learned. The symptoms of AD worsen over time, although the rate at which this occurs is known to be variable. Over time, MCI patients progress to Middle-Stage AD, also known as Moderate AD. A person with Middle-Stage AD will have forgetfulness of their own personal history, general confusion, changes in sleep patterns, as well as general behavioral and personality changes. Middle-Stage AD is generally the longest stage and may last for many years. Middle-Stage AD ultimately progresses to Late-Stage AD, also known as Severe AD. These individuals often require full-time care, and tend to lack lucidity, including loss of awareness of surroundings and recent experiences. Late-Stage AD results in changes in physical abilities, such as the ability to walk and swallow, and those individuals may become prone to opportunistic infection.

There are many problems with the current state of the art in detecting and diagnosing Early-Stage AD, especially at MCI and pre-clinical (pre-symptomatic) stages.

Alzheimer's disease is presented upon a clinical continuum that comprises preclinical stages, mild-cognitive impairment (MCI) stages, and full dementia. Early-Stage AD as defined herein comprises the pre-clinical and MCI stages of AD.

Pathological changes linked to AD, such as those associated with Early-Stage AD, are known to precede overt clinical symptoms for up to a decade prior to clinical diagnosis of AD. There is evidence as early as the preclinical stage of AD biomarkers such as low $A\beta_{42}$ serum levels, elevated CSF tau or phospho-tau, hypometabolism, cortical thinning/grey matter loss, as well as evidence of some subtle cognitive decline that does not rise to MCI levels. One point of agreement is that, in a high percentage of those afflicted, AD-related pathological changes begin in the brain 8-10 years before emergence of telltale symptoms.

This makes it difficult to identify AD patients at Early-Stage AD, at a time when treatments are most likely to be most beneficial. In view of this, intensive research is underway worldwide to discover and develop accurate, reliable and cost-effective methods for Early-Stage AD detection, including pre-clinical and MCI stages of AD, that can be widely implemented.

Limitations in the prior art include the requirement for lumbar spinal puncture to obtain CSF, which is considered somewhat invasive and not without risk. By contrast, procurement of blood is much less invasive, and plasma proteins, lipids as well as proteins and microRNAs enclosed within in exosomes and lysosomal derivatives have all been showing promise as biomarkers for early detection of AD pathology. Parallel advancements for early AD detection have been made in neuroimaging, such as MRI and positron emission tomography (PET) using radioactive tracers like Florbetapir (18F) and Pittsburgh compound B (PiB), and fluordeoxyglucose, but the high cost of these procedures and inconsistencies in interpretation prohibits their use as initial disease screeners, and they may not be readily available to individuals in economically disadvantaged areas or remote geographical locations.

Recently, much effort has been directed at identifying biomarkers in various body fluids, primarily in blood and CSF, which are useful for accurate detection of neurodegenerative diseases such as AD, preferably at early disease stages. CSF biomarkers have been extensively studied and include Aβ42, tau, phosphorylated tau. These have been shown to be quite sensitive and specific, even for early-stages of AD, but have the disadvantage of requiring spinal puncture for sample procurement. Blood-based biomarkers include various serum proteins and lipids as well as microR- NAs and proteins enclosed in blood-borne exosomes and other derivatives of lysosomes. Many of these are showing great promise, but more large-scale verification studies on these potential biomarkers are needed to establish their efficacy and disease specificity. Accordingly, there is an urgent need to identify biomarkers, such as autoantibodies, that can accurately detect and diagnose AD, including Early-Stage AD.

I. Early-Stage Alzheimer's Disease Autoantibody Biomarkers

"Early-Stage Alzheimer's Disease autoantibody biomarkers" or just "autoantibody biomarkers" is defined herein as compositions comprising at least one autoantibody biomarker that meet at least one of the following three criteria: i) is capable of detecting and specifically binding to at least one target antigen of the present invention; ii) is capable of serving as a diagnostic indicator that can be used to differentiate a subject having Early-Stage Alzheimer's Disease from a subject without AD or from a subject having Mid-Stage AD, and iii) presence of at least one autoantibody biomarker in a sample from a subject is capable of forming at least a part of a basis of a diagnosis of the subject as having Early-Stage AD.

It has been discovered herein that neurodegenerative diseases, including Early-Stage AD, cause the production and release of cellular products as a result of cell damage related to ongoing pathology, some of which are both cell type- and organ-specific. These released cellular products (many of which are proteins), their break-down fragments and disease-related post-translational modifications enter the blood and lymph circulation, act as antigens, and elicit an immune response. This immune response leads to the production and appearance of a relatively large number of self-reactive autoantibodies in the blood.

Cells throughout the body share a vast number of proteins in common, but only a relatively small subset of autoantibodies are specifically reactive to the cells, tissues and organs involved in a particular disease. It has been discovered in accordance with the present invention that this response leads to a disease-specific autoantibody profile that is characteristic for each disease and the specific cell types involved. In addition, in individuals with concurrent diseases, it has been discovered herein that a specific pattern of autoantibodies reflects each of these concurrent, ongoing disease processes. Accordingly, the present invention relates to the specific pattern of autoantibody biomarkers that are associated with Early-Stage Alzheimer's disease as well as the target antigens of the autoantibody biomarkers.

It has been discovered herein that autoantibodies capable of binding to brain-specific targets, including neurons and their supportive glial cells, are common in the blood; in fact they appear to be ubiquitous. Binding of these autoantibodies to neurons and/or glial cells in the brain is harmful to these cells and the functions in which they participate. It not only disrupts normal cellular functions, but also eventually leads to neuron and glial cell death and permanent loss from the brain.

Once inside the brain tissue, autoantibodies are free to bind selectively to any cells within the brain that possess and display the proper target antigens on their surfaces. If the autoantibody target is particularly abundant on a cell surface, the binding of many molecules of autoantibody can crosslink and immobilize this protein. If the target is an important receptor, the target and the cell can be rendered nonfunctional, leading to more global brain functional impairments. When the target cells are neurons, autoantibody binding may lead to neuronal dysfunction that can eventually manifest itself as behavioral, cognitive, memory and motor impairments. When the target is a glial cell that supports neurons, the loss of this support may indirectly compromise the function of neurons. Thus, specific brain-reactive autoantibodies in human sera can put one at risk for specific neurodegenerative diseases, such as Early-Stage AD. The invention described herein provides a method for the detection of these autoantibodies in human biological samples and their use as biomarkers for the detection and diagnosis of Early-Stage AD.

In accordance with the present invention, it has been discovered that brain-reactive autoantibodies are ubiquitous in the blood, and that these autoantibodies can enhance Aβ42 peptide deposition in the brain, a pathological hallmark of AD, including Early-Stage AD. It has further been discovered that brain-reactive autoantibodies are part of a much larger group of autoantibodies that are typically present in human sera, and that the expression of certain subsets of these autoantibodies is characteristically modulated by certain disease states such that disease-specific autoantibody patterns or profiles have been discovered and can be used as autoantibody biomarkers to detect and diagnose the presence of specific diseases such as Early-Stage AD. Among other embodiments, described herein is the use of these autoantibody biomarkers to accurately detect and diagnose Early-Stage AD based on their detection, identification and quantification revealed through interactions with their respective antigen targets on protein micro arrays.

Thus in one embodiment, the present invention provides a method of identifying a subject at risk for developing Early-Stage AD comprising obtaining an immunoglobulin-containing biological sample from the subject, performing an assay to determine the presence or absence of one or more Early-Stage AD autoantibody biomarker in the biological sample, and identifying the subject as at risk for developing Early-Stage AD if one or more of Early-Stage AD autoantibody biomarkers is present.

In another embodiment, the present invention provides a method for diagnosing Early-Stage AD in a subject in need of such diagnosis comprising obtaining an immunoglobulin-containing biological sample from the subject, performing an assay to determine the presence or absence of at least one autoantibody biomarker in the biological sample, and diagnosing Early-Stage AD if at least one Early-Stage AD autoantibody biomarker is present.

Another embodiment of this invention provides a method for detecting Early-Stage AD autoantibody biomarkers in a subject comprising obtaining an immunoglobulin-containing biological sample from the subject, and performing an assay to determine the presence or absence of one or more Early-Stage AD autoantibody biomarkers in the biological sample.

In a preferred embodiment of the invention, the immunoglobulin-containing biological sample is serum, plasma, whole blood, CSF, saliva, or sputum. A blood sample may be obtained by methods known in the art including venipuncture or a finger stick. CSF may be obtained by methods known in the art including a lumbar spinal tap. To obtain serum from blood, a sample of blood is received and centrifuged at a speed sufficient to pellet all cells and platelets, and the serum to be analyzed is drawn from the resulting supernatant. Sputum and saliva samples may be collected by methods known in the art. The biological samples may be diluted with a suitable buffer.

In a preferred embodiment of the invention, the assay used to determine the presence or absence of one or more Early-Stage AD autoantibody biomarkers in the biological sample is performed by contacting the biological sample with one or more target antigens that are specific for at least one Early-Stage AD autoantibody biomarker under conditions that allow an immunocomplex of the target antigen and the autoantibody biomarker to form, and detecting the presence of the immunocomplex.

Early-Stage AD autoantibody biomarkers may be identified by comparing the autoantibodies present in a immunoglobulin-containing sample from a subject having a neurodegenerative disease with autoantibodies present in an immunoglobulin-containing sample from an age-matched AD-free control subject. The target antigens for the autoantibody biomarkers present in the sample from the subject having Early-Stage AD, but present at lower levels or not at all in samples from control subjects, provide the identification of Early-Stage AD autoantibody biomarkers. The sample is preferably serum or plasma.

In a preferred embodiment of the invention, the subject is a human.

II. Early-Stage Alzheimer's Disease Autoantibody Biomarker Target Antigens

The terms "Early-Stage Alzheimer's Disease autoantibody biomarker target antigens" or just "target antigens" as used herein include, but are not limited to, protein and peptide antigens that are the target(s) for the Early-Stage Alzheimer's Disease autoantibody biomarkers of the present invention. The target antigens of the present invention are set forth below in Table 1, under the heading "Target Antigen," and are identified according to the art-accepted names.

Antigenic fragments of those target antigens disclosed in Table 1 are expressly considered covered by the present invention, so long as the autoantibody biomarkers of the present invention are capable of binding to the antigenic fragments thereof.

The heading "GenBank ID or Accession No." refers to publically available nucleotide and protein databases of the National Center for Biotechnology Information (NCBI), such as, for example, Accession No. or GenBank No., which are well-known and accessible to those of ordinary skill in the art. One of ordinary skill in the art will realize that by being given a GenBank No. or Accession No. corresponding to a nucleotide sequence, one may also find the corresponding publicly available amino acid/polypeptide sequence of the target antigen from that source. Thus, one of ordinary skill in the art will realize that if provided a GenBank No. or Accession No. corresponding to a nucleotide sequence, such as, but not limited to a cDNA clone or mRNA sequence that codes for a target antigen of the present invention, that one may find the target antigens of the present invention from the GenBank No. or Accession No. corresponding to said nucleotide sequence. Or, alternatively, one may simply transcribe (if DNA including cDNA) and translate (RNA) to provide a polypeptide corresponding to the target antigens of the present invention.

Target antigens may comprise a protein antigen or antigenic fragments thereof, a polypeptide or peptide fragment thereof containing one or more epitopes recognized by the autoantibody biomarkers, or an epitope peptidomimetic that is recognized by the autoantibody biomarkers. The target antigens may be purified from natural sources, or produced recombinantly or synthetically by methods known in the art, and may be in the form of fusion proteins. The target antigens may be produced in vitro using cell-free translation systems. In one preferred embodiment, the target antigens are produced in a mammalian, insect or bacterial expression system to ensure correct folding and function. All of these methods may be automated for high throughput production.

Suitable methods for external production and purification of target antigens to be spotted on arrays disclosed herein include expression in bacteria, as disclosed for example by Venkataram et al. (2008) *Biochemistry* 47:6590-6601, in yeast, as disclosed for example by Li et al. (2007) *Appl Biochem Biotechnol.* 142:105-124, in insect cells, as disclosed for example by Altman et al. (1999) *Glycoconj J* 16:109-123, and in mammalian cells, as disclosed for example by Spampinato et al. (2007) *Curr Drug Targets* 8:137-146.

One having ordinary skill in the art will understand that modifications, including substitutions, including but not limited to conservative substitutions, additions, and deletions may be made to the amino acid/polypeptide sequences of the target antigens of the present invention, and that the substituted target antigens would still be covered by the present invention, so long as the autoantibody biomarkers may still bind to the target antigens or antigenic fragments thereof.

One having ordinary skill in the art will understand that post-translational modifications may be made to the amino acid/polypeptide sequences of the target antigens of the present invention, and such modified target antigens would still be covered by the present invention, so long as the autoantibody biomarkers may still bind to the target antigens or antigenic fragments thereof.

One of ordinary skill in the art will understand that the target antigens include, but are not limited to, gene products, synthetic polypeptides, recombinant polypeptides, fragments of polypeptides, and analogs, orthologs, paralogs, or homologs of gene products, synthetic polypeptides, so long as the autoantibody biomarkers may still bind to the target antigens or antigenic fragments thereof.

One having ordinary skill in the art will understand that the target antigens may be chemically modified, such as but not limited to, e.g. modifications made to individual amino acid residues, PEG-ylation, addition of sequence tags, reporter molecules, so long as the autoantibody biomarkers may still bind to the target antigens.

So long as the autoantibody biomarkers bind to the target antigens or antigenic fragments thereof, any modification made to the target antigens or antigenic fragments thereof is considered to be covered by this invention.

TABLE 1

Early-Stage AD Autoantibody Biomarker Target Antigens

| GenBank ID or Accession No. | Target Antigen |
| --- | --- |
| BC022098.1 | cDNA clone MGC: 31944 IMAGE: 4878869, complete cds |
| BC020233.1 | cDNA clone MGC: 31936 IMAGE: 4765518, complete cds |
| BC015833.1 | cDNA clone MGC: 27152 IMAGE: 4691630, complete cds |
| NM_032855.1 | hematopoietic SH2 domain containing (HSH2D) |
| BC030984.1 | cDNA clone MGC: 32654 IMAGE: 4701898, complete cds |
| NM_016207.2 | cleavage and polyadenylation specific factor 3, 73 kDa (CPSF3) |
| BC016380.1 | cDNA clone MGC: 27376 IMAGE: 4688477, complete cds |
| PHC1705 | fms-related tyrosine kinase 3 ligand (FLT3LG) |
| BC051762.1 | Uncharacterized protein C20orf96 |
| NM_004987.3 | LIM and senescent cell antigen-like-containing domain protein 1 |

TABLE 1-continued

Early-Stage AD Autoantibody Biomarker Target Antigens

| GenBank ID or Accession No. | Target Antigen |
|---|---|
| PHC0205 | interleukin 20 (IL20) |
| PHC1346 | Recombinant Human Stromal Cell derived Factor-1a (SDF-1a) |
| XM_373800.2 | PREDICTED: *Homo sapiens* hypothetical LOC388528 (LOC388528) |
| BC010852.1 | Aflatoxin B1 aldehyde reductase member 2 |
| PHC1244 | chemokine (C-C motif) ligand 19 (CCL19) |
| NM_006428.3 | mitochondrial ribosomal protein L28 (MRPL28), nuclear gene encoding mitochondrial protein |
| BC053664.1 | zinc finger, FYVE domain containing 28 (ZFYVE28) |
| BC012104.1 | purinergic receptor P2Y, G-protein coupled, 2 (P2RY2) |
| NM_001290.1 | LIM domain binding 2 (LDB2) |
| NM_022491.2 | Sin3 histone deacetylase corepressor complex component SDS3 |
| BC029796.1 | hypothetical protein BC014011 (LOC116349) |
| NM_000159.2 | glutaryl-Coenzyme A dehydrogenase (GCDH), nuclear gene encoding mitochondrial protein, transcript variant 1 |
| NM_001098.2 | aconitase 2, mitochondrial (ACO2), nuclear gene encoding mitochondrial protein |
| NM_014763.2 | mitochondrial ribosomal protein L19 (MRPL19), nuclear gene encoding mitochondrial protein |
| NM_018282.1 | Paraspeckle component 1 |
| NM_005898.4 | cell cycle associated protein 1 (CAPRIN1), transcript variant 1 |
| XM_086879.4 | PREDICTED: *Homo sapiens* hypothetical LOC150371 (LOC150371) |
| BC104469.1 | Outer dense fiber protein 3-like protein 2 |
| BC032852.2 | melanoma antigen family B, 4 (MAGEB4) |
| NM_007255.1 | xylosylprotein beta 1,4-galactosyltransferase, polypeptide 7 (galactosyltransferase I) (B4GALT7) |
| NM_015891.2 | cell division cycle 40 homolog (S. cerevisiae) (CDC40) |
| NM_080548.1 | Tyrosine-protein phosphatase non-receptor type 6 |
| NM_006374.2 | serine/threonine kinase 25 (STE20 homolog, yeast) (STK25) |
| BC000468.1 | ubiquitin-conjugating enzyme E2 variant 1 (UBE2V1) |
| NM_182612.1 | Parkinson disease 7 domain containing 1 (PDDC1) |
| NM_001381.2 | docking protein 1, 62 kDa (downstream of tyrosine kinase 1) (DOK1) |
| thyroglobulin | NA |
| BC001304.1 | piccolo (presynaptic cytomatrix protein) (PCLO) |
| NM_017966.1 | vacuolar protein sorting 37 homolog C (S. cerevisiae) (VPS37C) |
| NM_003384.1 | vaccinia related kinase 1 (VRK1) |
| BC031068.1 | aminoadipate aminotransferase (AADAT) |
| BC030711.2 | Aprataxin and PNK-like factor |
| NM_024692.3 | CAP-GLY domain containing linker protein family, member 4 (CLIP4) |
| BC012423.1 | superoxide dismutase 2, mitochondrial (SOD2) |
| BC007852.1 | Serine/threonine-protein kinase 25 |
| NM_033377.1 | chorionic gonadotropin, beta polypeptide 1 [Source: RefSeq peptide; Acc: NP_203695] |
| NM_017451.1 | BAI1-associated protein 2 (BAIAP2), transcript variant 2 |
| BC056918.1 | glutathione S-transferase omega 2 (GSTO2) |
| 18S + 28S Ribosomal RNA | NA |
| NM_018357.2 | La ribonucleoprotein domain family, member 6 (LARP6), transcript variant 1 |
| NM_004732.1 | potassium voltage-gated channel, shaker-related subfamily, beta member 3 (KCNAB3) |
| PHG0046 | platelet-derived growth factor beta polypeptide (simian sarcoma viral (v-sis) oncogene homolog) (PDGFB), transcript variant 1 |
| BC030813.1 | cDNA clone MGC: 22645 IMAGE: 4700961, complete cds |
| NM_018039.2 | jumonji domain containing 2D (JMJD2D) |
| NM_022839.2 | mitochondrial ribosomal protein S11 (MRPS11), nuclear gene encoding mitochondrial protein, transcript variant 1 |
| NM_172160.1 | potassium voltage-gated channel, shaker-related subfamily, beta member 1 (KCNAB1), transcript variant 1 |
| BC017202.2 | Isovaleryl-CoA dehydrogenase, mitochondrial |
| BC017959.1 | chromosome 2 open reading frame 47 (C2orf47) |
| NM_014321.2 | origin recognition complex, subunit 6 like (yeast) (ORC6L) |
| BC067819.1 | transmembrane protein 29 (TMEM29) |
| NM_014431.1 | Paladin |
| NM_177437.1 | Taste receptor type 2 member 60 |
| NM_182536.2 | gastrokine 2 (GKN2) |
| NM_020633.2 | Vomeronasal type-1 receptor 1 |
| BC006206.2 | NIK and IKK{beta} binding protein (NIBP) |
| NM_004403.1 | deafness, autosomal dominant 5 (DFNA5) |
| BC031053.1 | lecithin retinol acyltransferase (phosphatidylcholine-retinol O-acyltransferase) (LRAT) |
| NM_004582.2 | Rab geranylgeranyltransferase, beta subunit (RABGGTB) |
| NM_181791.1 | Probable G-protein coupled receptor 141 |
| NM_002550.1 | Olfactory receptor 3A1 |
| NM_014926.2 | SLIT and NTRK-like protein 3 |
| BC015628.1 | 4-aminobutyrate aminotransferase (ABAT) |
| NM_007115.2 | tumor necrosis factor, alpha-induced protein 6 (TNFAIP6) |
| NM_004669.2 | chloride intracellular channel 3 (CLIC3) |
| NM_032861.2 | serine active site containing 1 (SERAC1) |
| BC062613.1 | sodium channel, nonvoltage-gated 1 alpha (SCNN1A) |
| BC009464.1 | Alpha-1,3-mannosyl-glycoprotein 4-beta-N-acetylglucosaminyltransferase B |
| BC098334.1 | RAP1, GTP-GDP dissociation stimulator 1 (RAP1GDS1), transcript variant 5, mRNA. |
| NM_175614.2 | NADH dehydrogenase (ubiquinone) 1 alpha subcomplex, 11, 14.7 kDa (NDUFA11) |
| PHC3016 | tumor necrosis factor (TNF superfamily, member 2) (TNF); see catalog number for detailed information on wild-type or point mutant status |
| BC031052.1 | TNF receptor-associated factor 6 (TRAF6) |

III. Specific Target Antigens

Specific target antigens of the present invention that may be of interest include, but are expressly not limited to, the following target antigens. These antigens are meant to be exemplary to assist one of ordinary skill in the art and are explicitly non-exclusive embodiments of the invention. One of ordinary skill in the art will realize that in relation to the sequence data presented below, substitutions, modifications, additions, and deletions may be made while retaining the functional characteristic of the target antigens, namely that the autoantibody biomarkers of the present invention remain capable of binding to the target antigens. This expressly includes, but is not limited to, any of the antigenic fragments disclosed below, so long as the autoantibody biomarkers of the present invention are capable of binding to the antigenic fragments.

A. BC022098.1—cDNA Clone MGC:31944 IMAGE: 4878869, Complete Cds

Target antigen MGC:31994 is derived from a sample comprising B-cells from tonsils in humans Target antigen MGC:31994 is known to have the following antigenic fragments, all of which are considered to be covered by this present invention as potential target antigens.

AA residues 26-130 "Immunoglobulin like region"; 29-131 "Immunoglobulin domain variable region (V); 29-130 "Immunoglobulin (Ig) lambda light chain variable (V) domain"; 43-44, 51-52 "L1 hypervariable region"; 51-53, 55, 112-113 "antigen binding site"; 57, 59, 106, 122 "heterodimer interface [polypeptide binding]"; 87-88, 92 "L2 hypervariable region"; 112-113, 119-121 "L3 hypervariable region"; 137-231 "Immunoglobulin domain constant region subfamily IGc"; 137-230 "Immunoglobulin Constant domain; cd07699, IgC_L"; 141-143, 156, 158, 160, 162-163, 185-188, 198-200 "heterodimer interface [polypeptide binding]"; 165, 190-191, 195 "intrachain IgV interface."

A nucleotide sequence coding for target antigen MGC:31944 is reproduced below:

SEQ ID NO: 1
```
CACAAGAGGCAGCACTCAGGACAATCTCCAGCATGGCCTGGTCTCCTCTC
CTCCTCACTCTCCTCGCTCACTGCACAGGGTCCTGGGCCCAGTCTGTGCT
GACGCAGCCGCCCTCAGTGTCTGGGGCCCCAGGGCAGAGGGTCACCATCT
CCTGCACTGGGAGCAGTTCCAACATCGGGGCAGGTTATGATGTACACTGG
TACCAGCAGCTTCCAGGAACAGCCCCCAAACTCCTCATCTATGGTAACAG
CAATCGGCCCTCAGGGGTCCCTGACCGATTCTCTGGCTCCAAGTCTGGCA
CCTCAGCCTCCCTGGCCATCACTGGGCTCCAGGCTGAGGATGAGGCTGAT
TATTACTGCCAATCCTATGACTACAGCCTGAGTGCTTCGGGGGTGTTCGG
CGGAGGGACCAAGCTGACCGTCCTAGGTCAGCCCAAGGCTGCCCCCTCGG
TCACTCTGTTCCCGCCCTCCTCTGAGGAGCTTCAAGCCAACAAGGCCACA
CTGGTGTGTCTCATAAGTGACTTCTACCCGGGAGCCGTGACAGTGGCCTG
GAAGGCAGATAGCAGCCCCGTCAAGGCGGGAGTGGAGACCACCACACCCT
CCAAACAAAGCAACAACAAGTACGCGGCCAGCAGCTACCTGAGCCTGACG
CCTGAGCAGTGGAAGTCCCACAGAAGCTACAGCTGCCAGGTCACGCATGA
AGGGAGCACCGTGGAGAAGACAGTGGCCCCTACAGAATGTTCATAGGTTC
TAAACCCTCACCCCCCCACGGGAGACTAGAGCTGCAGGATCCCAGGGGA
GGGGTCTCTCCTCCCACCCCAAGGCATCAAGCCCTTCTCCCTGCACTCAA
TAAACCCTCAATAAATATTCTCATTGTCAATCAAAAAAAAAAAAAAAAAA
AAAAAAAAAAAAAAAAAAA, Accession No. BC022098
```

An amino acid sequence for target antigen MGC:31944 is reproduced below:

SEQ ID NO: 2
```
MAWSPLLLTLLAHCTGSWAQSVLTQPPSVSGAPGQRVTISCTGSSSNIGA
GYDVHWYQQLPGTAPKLLIYGNSNRPSGVPDRFSGSKSGTSASLAITGLQ
AEDEADYYCQSYDYSLSASGVFGGGTKLTVLGQPKAAPSVTLFPPSSEEL
QANKATLVCLISDFYPGAVTVAWKADSSPVKAGVETTTPSKQSNNKYAAS
SYLSLTPEQWKSHRSYSCQVTHEGSTVEKTVAPTECS, Accession
No. AAH22098
```

B. BC020233.1—cDNA Clone MGC:31936 IMAGE: 4765518, Complete Cds

Target antigen MGC:31936 is derived from a sample comprising B-cells from tonsils in humans Target antigen MGC:31936 is known to have the following antigenic fragments, all of which are considered to be covered by this present invention as potential target antigens.

AA resides 26-130 "Immunoglobulin like region"; 29-131 "Immunoglobulin domain variable region (V); 29-130 "Immunoglobulin (Ig) lambda light chain variable (V) domain"; 43-44, 51-52 "L1 hypervariable region"; 51-53, 55, 112-113 "antigen binding site"; 57, 59, 106, 122 "heterodimer interface [polypeptide binding]"; 87-88, 91 "L2 hypervariable region"; 112-113, 116, 120-121 "L3 hypervariable region"; 137-121 "Immunoglobulin domain constant region subfamily IGc"; 137-230 "Immunoglobulin Constant domain cd07699, IgC_L"; 141-143, 156, 158, 160, 162-163, 185-188, 198-200 "heterodimer interface [polypeptide binding]"; 165, 190-191, 195 "intrachain IgV interface."

A nucleotide sequence (cDNA) coding for the target antigen MGC:31936 is reproduced below:

SEQ ID NO: 3
```
GGCATAAGAGGCAGCACTCAGGACAATCTCCAGCATGGCCTGGTCTCCTC
TCCTCCTCACTCTCCTCGCTCACTGCACAGGGTCCTGGGCCCAGTCTGTG
CTGACGCAGCCGCCCTCAGTGTCTGGGGCCCCAGGGCAGAGGGTCACCAT
CTCCTGCACTGGGAGCAGCTCCAACATCGGGGCAGGTTATGATGTACACT
GGTACCAGCAGCTTCCAGGAACAGCCCCCAAACTCCTCATCTATGGTAAC
AGCAATCGGCCCTCAGGGGTCCCTGACCGATTCTCTGGCTCCAAGTCTGG
CACCTCAGCCTCCCTGGCCATCACTGGGCTCCAGGCTGAGGATGAGGCTG
ATTATTACTGCCAGTCCTATGACAGCAGCCTGAGTGGTTTTGTGGTATTC
GGCGGAGGGACCAAGCTGACCGTCCTAGGTCAGCCCAAGGCTGCCCCCTC
GGTCACTCTGTTCCCGCCCTCCTCTGAGGAGCTTCAAGCCAACAAGGCCA
CACTGGTGTGTCTCATAAGTGACTTCTACCCGGGAGCCGTGACAGTGGCC
TGGAAGGCAGATAGCAGCCCCGTCAAGGCGGGAGTGGAGACCACCACACC
CTCCAAACAAAGCAACAACAAGTACGCGGCCAGCAGCTATCTGAGCCTGA
CGCCTGAGCAGTGGAAGTCCCACAGAAGCTACAGCTGCCAGGTCACGCAT
GAAGGGAGCACCGTGGAGAAGACAGTGGCCCCTACAGAATGTTCATAGGT
TCTCAACCCTCACCCCCCACCACGGGAGACTAGAGCTGCAGGATCCCAGG
GGAGGGGTCTCTCCTCCCACCCCAAGGCATCAAGCCCTTCTCCCTGCACT
CAATAAACCCTCAATAAATATTCTCATTGTCAATCAAAAAAAAAAAAAAA
AAA, Accession No. BC020233
```

An amino acid sequence for the target antigen MGC:31936 is reproduced below:

SEQ ID NO: 4
```
MAWSPLLLTLLAHCTGSWAQSVLTQPPSVSGAPGQRVTISCTGSSSNIGA
GYDVHWYQQLPGTAPKLLIYGNSNRPSGVPDRFSGSKSGTSASLAITGLQ
AEDEADYYCQSYDSSLSGFVVFGGGTKLTVLGQPKAAPSVTLFPPSSEEL
QANKATLVCLISDFYPGAVTVAWKADSSPVKAGVETTTPSKQSNNKYAAS
SYLSLTPEQWKSHRSYSCQVTHEGSTVEKTVAPTECS, Accession
No. AAH20233
```

C. NM_032855.1—Hematopoietic SH2 Domain Containing (HSH2D)

Target antigen Hematopoietic SH2 domain containing (HSH2D) is involved in tyrosine kinase signaling in hematopoietic cells. HSH2 is a target of both signaling pathways involved in T-cell activation, including recognition of antigen by T-cell receptor and a costimulatory signal provided primarily by CD28 in naïve T-cells. (Greene et al., 2003 [PubMed 12960172]). Target antigen Hematopoietic SH2 domain containing (HSH2D) is known to have the following antigenic fragments, all of which are considered to be covered by this present invention as potential target antigens.

AA residues 26-127 "Src homology 2 domain found in hematopoietic SH2 protein (SH2_HSH2_like)"; 41, 59, 79, 71 "phosphotyrosine binding pocket"; 80, 109 "hydrophobic binding pocket [polypeptide binding]."

A nucleotide sequence coding for the target antigen hematopoietic SH2 domain containing (HSH2D) is reproduced below:

SEQ ID NO: 5
GTCCTTCCCAAGACCACACCCAGGTCCAGTCATTCCCTAGGACTTGGCAG

AGAGCTGTACTCACAGCCAAGATCACAGCAAAATCAGCAAAGGGAAAAGG

CATGCAGAGTGAAGTCCAGAGGCAACCAGACAGAAGCATCCAGAATCCTC

TCACAGTGGGGTCACACACCCCATGCTTAACTCCCCCAACAATGAGTTGT

AACAACAGTCAGGTGTGGTGGTGTGTGCCTGTAGTCCCAGCTACTTGGGA

GCCTGAGGCAGGAGGATCACTTGAGTCCAGCAGTTCAAGACTGCAGTGAG

CTATGATCATACCACTGCACTCCAGCCTGAGTGACAGAGTGAAACTCTGT

CTCTAAAATAGGGCTCACCTGCTTGAGGAAACAGGAACTGCCTCGGGGCA

GCCAGCCCCGCCCCATTGACGTGCAGACCTTGAATCGAAACCCAGGCTCC

TGCAGGCACTGGCACAGCTACAGCGAGGGCCTCGGCCATCCAAGGGTCTC

CCAGGTGACCTTCCCTCCACCCCAGGAAGCTATGACAGAGGCCGGGAAGC

TGCCCCTACCGCTACCCCCACGGCTGGACTGGTTTGTGCACACCCAGATG

GGCCAGCTGGCCCAAGACGGGTCCCCGAGTGGTTCCATGGTGCAATCTC

AAGAGAGGATGCTGAGAACTTGCTGGAGTCACAGCCACTGGGATCCTTTC

TCATCAGGGTCAGTCACAGCCATGTGGGCTACACACTCTCCTACAAAGCC

CAAAGCAGCTGCTGCCATTTCATGGTGAAGCTCTTGGATGATGGGACTTT

CATGATCCCCGGGGAGAAGGTGGCCCACACCTCGCTGGACGCCCTGGTCA

CCTTCCACCAGCAGAAGCCAATTGAGCGCGCAGGGAGCTGCTGACACAG

CCCTGCAGGCAGAAGGATCCCGCAAACGTGGATTACGAGGATCTCTTCCT

CTACTCCAACGCAGTGGCCGAGGAAGCTGCCTGCCCGGTGTCTGCCCCTG

AGGAGGCCTCCCCAAAGCCAGTCCTGTGTCACCAATCAAAGGAAAGGAAG

CCGTCAGCAGAGATGAACAGAATAACCACCAAGGAAGCCACTTCCTCCTG

CCCCCCAAAATCCCCTCTTGGAGAGACCCGCCAGAAACTCTGGAGGAGCC

TCAAAATGCTCCCCGAGAGAGGCCAGAGGGTCCGGCAGCAGCTAAAAGC

CACCTCGCCACTGTGAACTTGTCGTCACTCTTGGATGTCCGGAGATCCAC

GGTGATCTCAGGCCCTGGGACCGGAAAAGGCAGCCAAGATCACTCAGGGG

ATCCCACCTCGGGGGACAGAGGCTACACGGATCCCTGTGTGGCCACATCT

CTCAAAAGCCCCTCACAGCCCCAGGCACCAAAAGACAGAAAGGTCCCCAC

CAGGAAGGCCGAGAGGTCGGTCAGCTGCATTGAGGTGACCCCAGGGGACA

GGAGTTGGCACCAAATGGTAGTGAGAGCCCTATCCTCCCAGGAGTCCAAG

CCAGAGCACCAGGGCTTGGCAGAGCCTGAGAACGACCAGCTCCCGGAGGA

GTACCAACAACCGCCACCCTTTGCCCCTGGGTACTGCTAGAGAACAGGTC

CACCCTGGCTCTGGGACTCGCTGCCAGGGGCTGCCACACTCCTGAATGCC

TTAACATTTCTTCCATGGCCCCACACCATGGCATCCGGGGGTCTTCGGGA

ACCCGGGAAATGGAATAAAGATGTTTTTGGGGTCTGTTCCTGCACTCACC

CATGGGGTGAGCTGGTTATTTTAGCAACAATCATCAGAGTGACGCTGATG

GTTTGGGGCACCAGCTATACATCAGCCCCAGTGCCAGACCTTCTATTCAT

TATTTTACGCCTCAGAGCAAGGCCCTCAGGGAGGGTCATCCTCCATGTTT

TGAAGAAGAGACTGAGGTTCAGAGAGGATAAGAGGCGTGACCAAGGCCAC

AGAGCTATGGGTGTCAGCACCAGGATTTGAAGCCAGGTGAATCCGAGCCC

TTTTCCCATATCATCTGTTTGTTCTGTTGTCTAAAAGCACACTGCAAGCC

GGGCTCAGTGGCTCATGCCTGTAGTCCCAGCACTCTGTGGGGCCGAGGCA

GGCAGATCGCTTGAGGTCAGGAGTTCGAGACCAGCCTGGCCAACATGGTG

AAACCCCGTCTATACTAAAAAATTCAAAAATTACCCGGACGTGGTGGCGC

ATGCCTGTAATCCCAGCTACTTGGGAGCCTGAGGCGGGAGAATTGCTTGA

ACCCGGGAGGCAGAGGTTGCAGTGAGCCGAGATCGCATCACTGCAGTCCA

GCCTGGATGACAGAGTGAGACTCCATCTCAAAAAATAAATAAATAAATAA

AAATGAAATTAAAAAATAAAAAAAAAAAAAAAAAAAAAAAAAAAAAAAAA

AAA, Accession No. NM_032855

An amino acid sequence for the target antigen hematopoietic SH2 domain containing (HSH2D) is reproduced below:

SEQ ID NO: 6
MTEAGKLPLPLPPRLDWFVHTQMGQLAQDGVPEWFHGAISREDAENLLES

QPLGSFLIRVSHSHVGYTLSYKAQSSCCHEMVKLLDDGTFMIPGEKVAHT

SLDALVTFHQQKPIEPRRELLTQPCRQKDPANVDYEDLFLYSNAVAEEAA

CPVSAPEEASPKPVLCHQSKERKPSAEMNRITTKEATSSCPPKSPLGETR

QKLWRSLKMLPERGQRVRQQLKSHLATVNLSSLLDVRRSTVISGPGTGKG

SQDHSGDPTSGDRGYTDPCVATSLKSPSQPQAPKDRKVPTRKAERSVSCI

EVTPGDRSWHQMVVRALSSQESKPEHQGLAEPENDQLPEEYQQPPPFAPG

YC, Accession No. NP_116244

D. BC056918.1—Glutathione S-Transferase Omega 2 (GSTO2)

Target antigen Glutathione S-transferase omega 2 (GSTO2) exhibits glutathione-dependent thiol transferase activity and participates in the biotransformation of inorganic arsenic and reduces monomethylarsonic acid. Target antigen Glutathione S-transferase omega 2 (GSTO2) is known to have the following antigenic fragments, all of which are considered to be covered by this present invention as potential target antigens.

AA residues 7-94 "Protein disulfide oxioreductases and other proteins with a thioredoxin fold (Thioredoxin_like)"; 26-111 "Glutathoine S-transferase [Posttraslational modification, protein turnover, chaperones], (GstA)"; 108-230 "C-terminal, alpha helical domain of Class Omega Glutathione S-ransferases; cd03184 (GST_C_Omega)"; 114-115, 118-119, 122, 153; "putative dimer interface [polypeptide binding]"; 121, 124-125, 128-129, 181, 184, 223 "substrate binding pocket (H-site) [chemical binding]"; 173, 176-177, 180, 183-184, 212, 216, 226, 230 "N-terminal domain interface [polypeptide binding]."

A nucleotide sequence coding for the target antigen glutathione S-transferase omega 2 (GSTO2) is reproduced below:

SEQ ID NO: 7
ACCACCTCTGCTGCCGCGCGCCTACCGGAGCCGCTTGGCCCTAGTGCTTT
CCAGCGGATTTCCCCTCAGGTGCGGAGCCGGGTGCCGGGGTCCCACAGCC
AACCACTACCGGTTCCTCTTTCGTCAGCCACCGGCGCCGGCAGGACCCGC
GAATCCCGATCTCCAGGAGCCTGTAAGGAGGCCGCCCATTGGCTCAGCCG
CACTGCTGGGCAGGTACTTCCAAAGCTTTGAGGATTGGCTGATGCTCTGG
GCGCCGGGGCTAGTTGGCGGGTAGGATCACGTGCGAGGGGCAGGCCCCGT
CTAGGCCCCGCCTCCTTGCTGCTGCTGCCGCCGCCAATCCTGGTCCGGTT
GCCCGAGTTCCCGGAGGTCTCTCGCGGGACCTCTCTCACCGCCACCGCTC
CTACTCTCGGGCTTCCAAATCTGGGGCGATGTCTCCCCAGGTTAAATTAC
CCTAGCTCCTGCTCCAGATCGCTTCCCCGTGCCCCGCCAGAGCCCAGTAG
TTCAAAAATTAAATTTGGGGCAAGGGGTGCGCGCCAGAGCGCAGCTGTTT
CTGGAGCCTGCGGCAGCGGTGGCGAGCCACAGGGCGGCGACCGTGAGCTC
CGGGAGCTGCGCAAACCACCTGGAGACCATGTCTGGGGATGCGACCAGGA
CCCTGGGGAAAGGAAGCCAGCCCCCAGGGCCAGTCCCGGAGGGGCTGATC
CGCATCTACAGCATGAGGTTCTGCCCCTATTCTCACAGGACCCGCCTCGT
CCTCAAGGCCAAAGACATCAGACATGAAGTGGTCAACATTAACCTGAGAA
ACAAGCCTGAATGGTACTATACAAAGCACCCTTTTGGCCACATTCCTGTC
CTGGAGACCAGCCAATGTCAACTGATCTATGAATCTGTTATTGCTTGTGA
GTACCTGGATGATGCTTATCCAGGAAGGAAGCTGTTTCCATATGACCCTT
ATGAACGAGCTCGCCAAAAGATGTTATTGGAGCTATTTTGTAAGGTCCCA
CATTTGACCAAGGAGTGCCTGGTAGCGTTGAGATGTGGGAGAGAATGCAC
TAATCTGAAGGCAGCCCTGCGTCAGGAATTCAGCAACCTGGAAGAGATTC
TTGAGTATCAGAACACCACCTTCTTTGGTGGAACCTGTATATCCATGATT
GATTACCTCCTCTGGCCCTGGTTTGAGCGGCTGGATGTGTATGGGATACT
GGACTGTGTGAGCCACACGCCAGCCCTGCGGCTCTGGATATCAGCCATGA
AGTGGGACCCCACAGTCTGTGCTCTTCTCATGGATAAGAGCATTTTCCAG
GGCTTCTTGAATCTCTATTTTCAGAACAACCCTAATGCCTTTGACTTTGG
GCTGTGCTGAGTCTCACTGTCCACCCCTTCGCTGTCCAGAATTCCCCAGC
TTGTTGGGAGTCTACGTCACGGCTTGTCTTGGGAACCAATCCGTCTCTCT
TTCTTTTCTTTGAAGTTCCCAATAAAATGAAAACAGGAAATGTAAAAAAA
AAAAAAAAAAAAAAAAAAAAAAAAAAAAAAAAAAAAAAAAAAAA,
Accession No. BC056918

An amino acid sequence for the target antigen glutathione S-transferase omega 2 (GSTO2) is reproduced below:

SEQ ID NO: 8
MSGDATRTLGKGSQPPGPVPEGLIRIYSMRFCPYSHRTRLVLKAKDIRHE
VVNINLRNKPEWYYTKHPFGHIPVLETSQCQLIYESVIACEYLDDAYPGR
KLFPYDPYERARQKMLLELFCKVPHLTKECLVALRCGRECTNLKAALRQE
FSNLEEILEYQNTTFFGGTCISMIDYLLWPWFERLDVYGILDCVSHTPAL
RLWISAMKWDPTVCALLMDKSIFQGFLNLYFQNNPNAFDFGLC,
Accession No. AAH56918

E. BC015833.1—cDNA Clone MGC:27152 IMAGE: 4691630, Complete Cds

Target antigen MGC:27152 is derived from a sample comprising lung cells in humans Target antigen MGC:27152 is known to have the following antigenic fragments, all of which are considered to be covered by this present invention as potential target antigens.

AA residues 26-128 "Immunoglobulin like region"; 29-128 "Immunoglobulin domain"; 29-112 "Immunoglobulin domain variable region (V)"; 135-229 "Immunoglobulin domain constant region subfamily (IGc)"; 135-228 "Immunoglobulin constant domain; cd07699"; 139-141, 154, 156, 158, 160-161, 183-186, 196-198 "heterodimer interface [polypeptide binding]"; 163, 188-189, 193 "intrachain IgV interface."

A nucleotide sequence coding for the target antigen MGC:27152 is reproduced below:

SEQ ID NO: 9
GGGGGGGGTCACAAGAGGCAGCGCTCTCGGGACGTCTCCACCATGGCCTG
GGCTCTGCTGCTCCTCACTCTCCTCACTCAGGACACAGGGTCCTGGGCCC
AGTCTGCCCTGACTCAGCCTGCCTCCGTGTCTGGGTCTCCTGGACAGTCG
ATCACCATCTCCTGCACTGGAACCAGCACTGATGTTGGGAGTCATAGCCT
TGTCTCCTGGTACCAACAGCACCCAGGCAAAGCCCCCAAATTTCTTATTT
TCGAGGGCAGTAAGCGGCCCTCAGGGGTTTCGAATCGCTTCTCTGGCTCC
AAGTCTGGCAACACGGCCTCCCTGACAATCTCTGGGCTCCAGGCTGAGGA
CGAGGCTGATTATTACTGCTGTTCATATGTTGGTAGTGGCACTGTGGTTT
TCGGCGGAGGGACGAAGCTGACCGTCCTAGGTCAGCCCAAGGCTGCCCCC
TCGGTCACTCTGTTCCCGCCCTCCTCTGAGGAGCTTCAAGCCAACAAGGC
CACACTGGTGTGTCTCATAAGTGACTTCTACCCGGGAGCCGTGACAGTGG
CCTGGAAGGCAGATAGCAGCCCCGTCAAGGCGGGAGTGGAGACCACCACA
CCCTCCAAACAAAGCAACAACAAGTACGCGGCCAGCAGCTATCTGAGCCT
GACGCCTGAGCAGTGGAAGTCCCACAGAAGCTACAGCTGCCAGGTCACGC
ATGAAGGGAGCACCGTGGAGAAGACAGTGGCCCCTACAGAATGTTCATAG
GTTCTCAACCCTCACCCCCACCAGCGGAGACTAGAGCTGCAGGATCCCAG
GGGAGGGGTCTCTCCTCCCACCCCAAGGCATCAAGCCCTTCTCCCTGCAC
TCAATAAACCCTCAATAAATATTCTCATTGTCAAGCAAAAAAAAAAAAA
AAAAAAAAAAAAAA, Accession No. BC015833

An amino acid sequence for the target antigen MGC:27152 is reproduced below:

SEQ ID NO: 10
MAWALLLLTLLTQDTGSWAQSALTQPASVSGSPGQSITISCTGTSTDVGS
HSLVSWYQQHPGKAPKFLIFEGSKRPSGVSNRFSGSKSGNTASLTISGLQ
AEDEADYYCCSYVGSGTVVFGGGTKLTVLGQPKAAPSVTLFPPSSEELQA

-continued

NKATLVCLISDFYPGAVTVAWKADSSPVKAGVETTTPSKQSNNKYAASSY

LSLTPEQWKSHRSYSCQVTHEGSTVEKTVAPTECS, Accession No. AAH15833

IV. Protein Microarrays

Protein microarrays containing thousands of full-sized or nearly full-sized human proteins spotted on a single specimen slide may be used to identify autoantibodies in a patient sample that are reactive with the antigen targets on the microarray. Autoantibody biomarkers in a control sample may be similarly identified. The patient autoantibody profile may be compared with the control autoantibody profile to identify those linked directly to the disease (i.e., Early-Stage AD autoantibody biomarkers) and corresponding target antigens.

Protein microarrays useful for identifying Early-Stage AD autoantibody biomarkers and target antigens may be made by methods known in the art and are also commercially available. Commercially available protein microarrays include, for example, Invitrogen's Prot® Array® Human Protein Microarray v5.0, which is preferably used in accordance with the Invitrogen ProtoArray® protocol and Immune Response Biomarker Profiling application.

Methods for probing and scanning such protein microarrays, and for determining the diagnostic significance of the resulting data, are known to those of skill in the art and disclosed, for example, by Tibshirani et al. (2002) *Proc Natl Acad Sci USA* 99, 6567-6572.

Once the Early-Stage AD autoantibody biomarkers are identified by the methods disclosed in the present invention, the corresponding target antigens are identified and selected for use in the methods of detection and diagnosis.

Assays and conditions for the detection of immunocomplexes are known to those of skill in the art. Such assays include, for example, competition assays, direct reaction assays and sandwich-type assays. The assays may be quantitative or qualitative. In one preferred embodiment, the assay utilizes a solid phase or substrate to which the target antigens are directly or indirectly attached, such as a microtiter or microassay plate, slide, magnetic bead, non-magnetic bead, column, matrix, membrane, or sheet, and may be composed of a synthetic material such as polystyrene, polyvinyl chloride, polyamide, or other synthetic polymers, natural polymers such as cellulose, derivatized natural polymers such as cellulose acetate or nitrocellulose, and glass, for example glass fibers. The substrate preferably comprises a plurality of individually addressable target antigens immobilized on the surface. The individually addressable target antigens are preferably immobilized on the surface to form an array. The substrates may be used in suitable shapes, such as films, sheets, or plates, or may be coated onto or bonded or laminated to appropriate inert carriers, such as paper, glass, plastic films, or fabrics. In a preferred embodiment, the substrate is a slide or a bead.

Methods for attaching the target antigens to the support or substrate are known in the art and include covalent and noncovalent interactions. For example, diffusion of applied proteins into a porous surface such a hydrogel allows noncovalent binding of unmodified protein within hydrogel structures. Covalent coupling methods provide a stable linkage and may be applied to a range of proteins. Biological capture methods utilizing a tag (e.g., hexahistidine/Ni-NTA or biotin/avidin) on the protein and a partner reagent immobilized on the surface of the substrate provide a stable linkage and bind the protein specifically and in reproducible orientation.

In one preferred embodiment, the target antigens are coated or spotted onto the support or substrate such as chemically derivatized glass.

In one preferred embodiment the target antigens are provided in the form of an array, and preferably a microarray. Protein microarrays are known in the art and reviewed for example by Hall et al. (2007) *Mech Ageing Dev* 128: 161-167 and Stoevesandt et al (2009) *Expert Rev Proteomics* 6:145-157, the disclosures of which are incorporated herein by reference. Microarrays may be prepared by immobilizing purified target antigens on a substrate such as a treated microscope slide using a contact spotter or a non-contact microarrayer. Microarrays may also be produced through in situ cell-free synthesis directly from corresponding DNA arrays.

Suitable methods for in situ ("on-chip") protein production are disclosed, for example, by Ramachandran et al. (2006) *Methods Mol. Biol* 2328:1-14 and He et al. (2008) *Curr. Opin Biotechnol* 19:4-9.

Other methods by which proteins are simultaneously expressed and immobilized in parallel on an array surface are also known in the art and may be used in accordance with the present invention. For example, in the Protein In Situ Arrays (PISA) method (He et al. (2001) *Nucleic Acids Res* 29:e73), proteins are made directly from DNA, either in solution or immobilized, and become attached to the array surface as they are made through recognition of a tag sequence. The proteins are expressed in parallel in vitro utilizing a cell free system, commonly rabbit reticulocyte or *E. coli* S30, to perform coupled transcription and translation. In this method, protein expression is performed on a surface which is precoated with an immobilizing agent capable of binding to the tag. Thus after each protein is translated, it becomes fixed simultaneously and specifically to the adjacent surface, while the other materials can subsequently be washed away. Microarrays are produced directly onto glass slides, either by mixing the DNA with the cell free lysate system before spotting or by a multiple spotting technique (MIST) in which DNA is spotted first followed by the expression system.

In the system known as Nucleic Acid Programmable Protein Array (NAPPA) (Ramachandran et al. (2004) *Science* 305:86-90), transcription and translation from an immobilized (as opposed to a solution) DNA template allow conversion of DNA arrays to protein arrays. In this method, biotinylated cDNA plasmids encoding the proteins as GST fusions are printed onto an avidin-coated slide, together with an anti-GST antibody acting as the capture entity. The cDNA array is then covered with rabbit reticulocyte lysate to express the proteins, which become trapped by the antibody adjacent to each DNA spot, the proteins thereby becoming immobilized with the same layout as the cDNA. This technology generates a protein array in which the immobilized proteins are present together with DNA and a capture agent.

Another suitable method for generating a protein array is the DNA Array to Protein Array (DAPA) method. This method for in situ protein arraying uses an immobilized DNA array as the template to generate 'pure' protein arrays on a separate surface from the DNA, and also can produce multiple copies of a protein array from the same DNA template (He et al. (2008) *Nature Methods*, 5:175-7). Cell-free protein synthesis is performed in a membrane held between two surfaces (e.g., glass slides), one of which is arrayed with DNA molecules while the other surface carries a specific reagent to capture the translated proteins. Individual, tagged proteins are synthesized in parallel from the arrayed DNA, diffuse across the gap and are subsequently immobilized through interaction with the tag-capturing reagent on the opposite surface to form a protein array. Discrete spots which accurately reflect the DNA in position and quantity are produced. Replicate copies of the protein array can be obtained by reuse of the DNA.

Array fabrication methods include robotic contact printing, ink-jetting, piezoelectric spotting and photolithography. For example, purified target antigens of the invention that are produced and purified externally may be spotted onto a microarray substrate using a flexible protein microarray inkjet printing system (e.g., ArrayJet, Roslin, Scotland, UK) to provide high quality protein microarray production. The precise rows and columns of target antigens may be converted to detectable spots denoting both the presence and amount of serum autoantibody biomarkers that have been bound.

The production of the microarrays is preferably performed with commercially available printing buffers designed to maintain the three-dimensional shape of the target antigens. In one preferred embodiment, the substrate for the microarray is a nitrocellulose-coated glass slide.

The assays are performed by methods known in the art in which the one or more target antigens are contacted with the biological sample under conditions that allow the formation of an immunocomplex of a target antigen and an antibody, and detecting the immunocomplex. The presence and amount of the immunocomplex may be detected by methods known in the art, including label-based and label-free detection. For example, label-based detection methods include addition of a secondary antibody that is coupled to an indicator reagent comprising a signal generating compound. The secondary antibody may be an anti-human IgG or IgM antibody. Indicator reagents include chromogenic agents, catalysts such as enzyme conjugates, fluorescent compounds such as fluorescein, rhodamine and AlexaFluor, chemiluminescent compounds such as dioxetanes, acridiniums, phenanthridiniums, ruthenium, and luminol, radioactive elements, direct visual labels, as well as cofactors, inhibitors and magnetic particles. Examples of enzyme conjugates include alkaline phosphatase, horseradish peroxidase and beta-galactosidase. Methods of label-free detection include surface plasmon resonance, carbon nanotubes and nanowires, and interferometry. Label-based and label-free detection methods are known in the art and disclosed, for example, by Hall et al. (2007) and by Ray et al. (2010) *Proteomics* 10:731-748. Detection may be accomplished by scanning methods known in the art and appropriate for the label used, and associated analytical software.

In one preferred embodiment of the present invention, fluorescence labeling and detection methods are used to detect the immunocomplexes. Commercially available slide scanners (e.g. the Genepix 4000B slide scanner (Molecular Devices, Inc.) with associated analytical software may be used. In one preferred embodiment, the immunocomplex is probed with fluorescent-labeled (e.g., Alexa-Fluor (Invitrogen) anti-human antibody and the intensity of fluorescence at each protein spot is measured using a microarray scanner. Commercially available software (e.g. GenePix Pro 5.0 software (Axon instruments) may be used to extract the net median pixel intensities for individual features from the digital images produced by the scanner. Data may be normalized by comparing median values of multiple identical control spots in different regions of the same array.

Detection of diagnostic immunocomplexes is indicative of the presence of Early-Stage AD autoantibody biomarkers in the biological sample, and thus a positive diagnosis of Early-Stage AD or detection of patients at risk of developing AD. The quantity and quality of immunocomplexes formed can further guide those of ordinary skill in the art as to how advanced the conditions may be or a suitable therapeutic strategy.

In another embodiment, the present invention provides a method of generating a patient-specific Early-Stage AD autoantibody biomarker profile comprising obtaining a serum-containing biological sample from a patient, performing an assay to determine the presence or absence of Early-Stage AD autoantibody biomarkers in the biological sample, and generating a patient-specific Early-Stage AD biomarker profile of the AD autoantibody biomarkers present in the sample. The assay is performed as described hereinabove.

The results of the assay provide an Early-Stage AD autoantibody biomarker profile for the patient that is useful to diagnose Early-Stage AD and optimize a treatment regimen for Early-Stage AD.

In another embodiment, the present invention provides a method of identifying a subject at risk for developing Early-Stage AD comprising obtaining an immunoglobulin-containing biological sample from the subject, performing an assay to determine the presence or absence of one or more Early-Stage AD autoantibody biomarkers in the biological sample, and identifying the subject as at risk for developing Early-Stage AD if one or more of the Early-Stage AD autoantibody biomarkers is present. The assay is performed as described herein above.

In yet another embodiment, the present invention provides a substrate on which one or more target antigens that are specific for an Early-Stage AD autoantibody biomarker are immobilized. The present invention also provides, in another embodiment, a microarray comprising a substrate on which one or more target antigens that are specifically bound by an Early-Stage AD autoantibody biomarker are immobilized. The substrates and microarrays may be made as described hereinabove and are useful for creating Early-Stage AD autoantibody biomarker profiles and for the diagnosis of Early-Stage AD. A target antigen may comprise a protein antigen of Table 1, or a polypeptide or peptide fragment thereof containing one or more epitopes recognized by the Early-Stage AD autoantibody biomarker, or an epitope peptidomimetic that is recognized by the Early-Stage AD autoantibody biomarker. Peptidomimetics include, for example, D-peptides, peptoids, and β-peptides. The substrate and microarrays may contain, as the target antigen, at least one of the protein antigens of Table 1 or fragments thereof containing one or more epitopes recognized by the Early-Stage AD autoantibody biomarker.

In another embodiment, the substrate and microarrays may contain, as the target antigen, at least one of the protein antigens of Table 2, or a polypeptide or peptide fragment thereof containing one or more epitopes recognized by the Early-Stage AD autoantibody biomarker, or an epitope peptidomimetic that is recognized by the Early-Stage AD autoantibody biomarker. Peptidomimetics include, for example, D-peptides, peptoids, and β-peptides. The protein antigens in Tables 2-5 are identified by art-accepted names as well as database identification numbers. The database identification numbers refer to the publically available protein databases of the National Center for Biotechnology Information (NCBI) which is well-known and accessible to those of ordinary skill in the art.

One embodiment of the invention is directed to a method for detecting early-stage Alzheimer's disease diagnostic autoantibodies in a subject in need thereof comprising: (a) obtaining an immunoglobulin-containing biological sample from the subject, and (b) performing an assay on the biological sample to determine the presence of autoantibodies in the biological sample, where the assay comprises the steps of: (i) forming immunocomplexes between autoantibodies targeting at least two antigens, at least 3 antigens, at least 4 antigens or all 5 antigens selected from the group consisting BC053664.1, BC012104.1, BC029796.1, NM_000159.2, and NM_001098.2; and (ii) detecting the presence of the immunocomplexes.

Another embodiment of the invention is directed to a method of generating a subject-specific, early-stage Alzheimer's disease-specific autoantibody profile comprising: (a) obtaining an immunoglobulin-containing biological sample from a subject, (b) performing an assay on the biological sample to determine the presence more than one early-stage Alzheimer's disease diagnostic autoantibodies in the biological sample, where the assay comprises the steps of: (i) forming immunocomplexes between autoantibodies targeting at least two antigens, at least 3 antigens, at least 4 antigens or all 5 antigens selected from the group consisting of BC053664.1, BC012104.1, BC029796.1, NM_000159.2, and NM_001098.2; (ii) detecting the presence of the immunocomplexes; and (c) generating a subject-specific early-stage Alzheimer's disease-specific autoantibody profile of the autoantibodies present in the sample and optionally initiate a customized treatment regimen. In one embodiment, the methods are directed for human subjects. In another embodiment, the methods can be directed to a biological sample selected from the group consisting of whole blood, serum, cerebrospinal fluid, saliva, and sputum.

The methods are also directed to the antigens being attached to a substrate and which are in the form of an array; the array can be a microarray. The methods can also be directed to a substrate which is a nitrocellulose-coated glass slide. The microarray can further contain an additional antigen selected from the group consisting of BC022098.1, BC020233.1, BC015833.1, NM_032855.1, BC030984.1, NM_016207.2, BC016380.1, BC051762.1, and PHC1244. The microarray can further contain an additional antigen selected from the group consisting of PHC1346, XM_373800.2, NM_014763.2, NM_018282.1, XM_086879.4, BC104469.1, BC032852.2, NM_007255.1, NM_015891.2, NM_080548.1, NM_006374.2, BC000468.1, NM_182612.1, NM_001381.2, thyroglobulin, BC001304.1, NM_017966.1, NM_003384.1, BC031068.1, BC030711.2, NM_024692.3, BC012423.1, BC007852.1, NM_033377.1, NM_017451.1, BC056918.1, 18S+28S Ribosomal RNA, NM_018357.2, NM_004732.1, PHG0046, BC030813.1, NM_018039.2, NM_022839.2, NM_172160.1, BC017202.2, and BC017959.1.

In addition to detecting the presence of immunocomplexes between autoantibodies targeting at least two or three or four or five of BC053664.1, BC012104.1, BC029796.1, NM_000159.2, and NM_001098.2, the methods in accordance to the present invention can further include formation of immunocomplexes between at least one additional antigen selected from the group consisting BC022098.1, BC020233.1, BC015833.1, NM_032855.1, BC030984.1, NM_016207.2, BC016380.1, BC051762.1, and PHC1244, and the autoantibodies present in the sample. The formation of these immunocomplex is further detected by those methods conventionally known in the art.

In another embodiment, detecting the presence of immunocomplexes between autoantibodies targeting at least two or three or four or five of BC053664.1, BC012104.1, BC029796.1, NM_000159.2, and NM_001098.2, the methods in accordance to the present invention can further include formation of immunocomplexes between at least one additional antigen selected from the group consisting PHC1346, XM_373800.2, NM_014763.2, NM_018282.1, XM_086879.4, BC104469.1, BC032852.2, NM_007255.1, NM_015891.2, NM_080548.1, NM_006374.2, BC000468.1, NM_182612.1, NM_001381.2, thyroglobulin, BC001304.1, NM_017966.1, NM_003384.1, BC031068.1, BC030711.2, NM_024692.3, BC012423.1, BC007852.1, NM_033377.1, NM_017451.1, BC056918.1, 18S+28S Ribosomal RNA, NM_018357.2, NM_004732.1, PHG0046, BC030813.1, NM_018039.2, NM_022839.2, NM_172160.1, BC017202.2, and BC017959.1. Further the formation of these immunocomplex is detected.

Another embodiment of the invention is directed to a kit or an article of manufacture for detecting AD or early-stage Alzheimer's disease (ESAD) diagnostic biomarkers comprising: a) a combination of antigens comprising BC022098.1, BC020233.1, BC015833.1, NM_032855.1, BC030984.1, NM_016207.2, BC016380.1, BC051762.1, PHC1346, XM_373800.2, PHC1244, BC053664.1, BC012104.1, BC029796.1, NM_000159.2, NM_001098.2, NM_014763.2, NM_018282.1, XM_086879.4, BC104469.1, BC032852.2, NM_007255.1, NM_015891.2, NM_080548.1, NM_006374.2, BC000468.1, NM_182612.1, NM_001381.2, thyroglobulin, BC001304.1, NM_017966.1, NM_003384.1, BC031068.1, BC030711.2, NM_024692.3, BC012423.1, BC007852.1, NM_033377.1, NM_017451.1, BC056918.1, 18S+28S Ribosomal RNA, NM_018357.2, NM_004732.1, PHG0046, BC030813.1, NM_018039.2, NM_022839.2, NM_172160.1, BC017202.2, BC017959.1 (see Table 5); b) assay reagents for detection of at least two immunocomplexes formed by binding of the antigens to the ESAD diagnostic biomarkers in an immunoglobulin-containing biological sample, and c) a package labeling.

The package labeling can include instructions indicating: i) a diagnosis of ESAD or a degree of risk associated in a subject upon detecting formation of at least two, three or four immunocomplexes between antigens selected from the group consisting of BC053664.1, BC012104.1, BC029796.1, NM_000159.2, and NM_001098.2; and AD diagnostic biomarkers corresponding to antigens obtained from the immunoglobulin-containing biological sample; and/or instructions indicating ii) at least a 90% risk of developing Alzheimer's disease within the next 1 to 10 years when simultaneous immunocomplex formation is detected for, two, three, four or all of BC053664.1, BC012104.1, BC029796.1, NM_000159.2, and NM_001098.2.

In one embodiment, the risk of developing Alzheimer's disease can be about 90% or between 80 to 95% or 85 to 95% or about 96 to 99% or any range falling therein. For the purposes of the present application the term "about" means ±5% of the value. The onset of Alzheimer's disease can be within about 1, or about 2, or about 3, or about 4, or about 5, or about 6, or about 7, or about 8, or about 9, or about 10 years, and can be about 1 to 2, or about 1 to 3, or about 1 to 5, or about 1 to 7, or about 1 to 9, or about 2 to 3, or about 2 to 4, or about 2 to 5, or about 2 to 7, or about 2 to 9, or about 2 to 10, or about 3 to 4, or about 3 to 5, or about 3 to 7, or about 3 to 9, or about 3 to 10, or about 4 to 5, or about 4 to 6, or about 4 to 8 or about 4 to 10 years, or any range falling therein. In the kit the target antigens can be immobilized on a substrate. In the kit the antigens disclosed in the package labeling i) can further contain an additional antigen selected from the group consisting of BC022098.1, BC020233.1, BC015833.1, NM_032855.1, BC030984.1, NM_016207.2, BC016380.1, BC051762.1, and PHC1244. In the kit the antigens disclosed in the package labeling i) can further contain an additional antigen selected from the group consisting of PHC1346, XM_373800.2, NM_014763.2, NM_018282.1, XM_086879.4, BC104469.1, BC032852.2, NM_007255.1, NM_015891.2, NM_080548.1, NM_006374.2, BC000468.1, NM_182612.1, NM_001381.2, thyroglobulin, BC001304.1, NM_017966.1, NM_003384.1, BC031068.1, BC030711.2, NM_024692.3, BC012423.1, BC007852.1, NM_033377.1, NM_017451.1, BC056918.1, 18S+28S Ribosomal RNA, NM_018357.2, NM_004732.1, PHG0046, BC030813.1, NM_018039.2, NM_022839.2, NM_172160.1, BC017202.2, and BC017959.1.

In some embodiments, the assay is designed to determine the presence or absence of at least one, two, three or four AD autoantibody biomarker using between one (1) to ten (10) (inclusive) target antigens from Table 1 or antigenic fragments thereof. In another embodiment, the assay determines the presence or absence of at least one, two, three, four Early-Stage AD autoantibody biomarker using between five (5) and ten (10) (inclusive) target antigens from Table 1 or antigenic fragments thereof. In another embodiment, autoantibody biomarker are between one (1) and twenty five (25) (inclusive) target antigens from Table 1 or antigenic fragments thereof. In yet another embodiment, the assay determines the presence or absence of at least ten Early-Stage AD autoantibody biomarker using between ten (10) and fifty (50) (inclusive) target antigens from Table 1 or antigenic fragments thereof.

In the kit the package labeling can indicate a diagnosis of ESAD, or quantify the risk of developing AD upon positive detection. In another embodiment, the kit can provide a treatment regimen, if at least two, at least three, or at least four, or all five of said biomarkers in said biological sample are detected. In at least one embodiment, the package labeling is not limited to instruction of use, rather, provides an interpretation of the structural information provided upon the proper use of the microarray components of the kit. In another embodiment, the package labeling provides the patient's risk of developing AD in 1, 2, 3, 4, 5, 6, 7, 8, 9 or 10 years from the date of detection of the immunocomplexes. In another embodiment, the package labeling includes classification of the patient's risk of developing AD. In another embodiment, patient's risk of developing AD and any classification of such patients are described in the packaging in conjunction with the presence of signs, symptoms, or phenotype associated with AD. Thus, in one embodiment combination of immunocomplex formation and such signs, symptoms or phenotypes as memory loss, mood disorder, confusion, speaking abilities or the like, provides prognosis or quantifies the risk of developing AD.

Analytics

In further embodiments, the present invention provides for diagnostic systems for detecting neurodegenerative disease diagnostic autoantibodies in a subject at risk for developing neurodegenerative disease, such as Early-Stage AD. This diagnostic system may comprise any of the methods, compositions, or diagnostic assays disclosed herein, and may further comprise analysis and generation of data, for example but not necessarily limited to, data that relates to the risk of a patient developing a particular neurodegenerative disease, such as Early-Stage AD. Based on this data, a treatment plan may be generated or an existing treatment plan may be optimized. This diagnostic system may involve data generation by use of computational algorithm(s), for example those described in U.S. Patent Publication No. US 2013/0157888, incorporated by reference herein in its entirety.

Generally, the diagnostic systems involve steps of (a) obtaining an immunoglobulin-containing biological sample from the subject, (b) conducting an immunoassay to detect at least five target antigens or antigenic fragments thereof specific for said neurodegenerative disease, (c) detecting the presence or absence of an immunocomplex, wherein the presence of an immunocomplex is indicative of the presence of the autoantibody biomarker in said patient and wherein the absence of an immunocomplex is indicative of the absence of autoantibody biomarkers, and (d) generating a report identifying the risk of said patient in developing said neurological condition, and optionally, (e) optimizing the treatment plan in patients in need thereof.

EXAMPLES

See DeMarshall, et al., Alzheimer's & Dementia: Diagnosis, Assessment & Disease Monitoring, 2016, 3, pp 51-62.

Example 1

A. Overview

Figure 7:
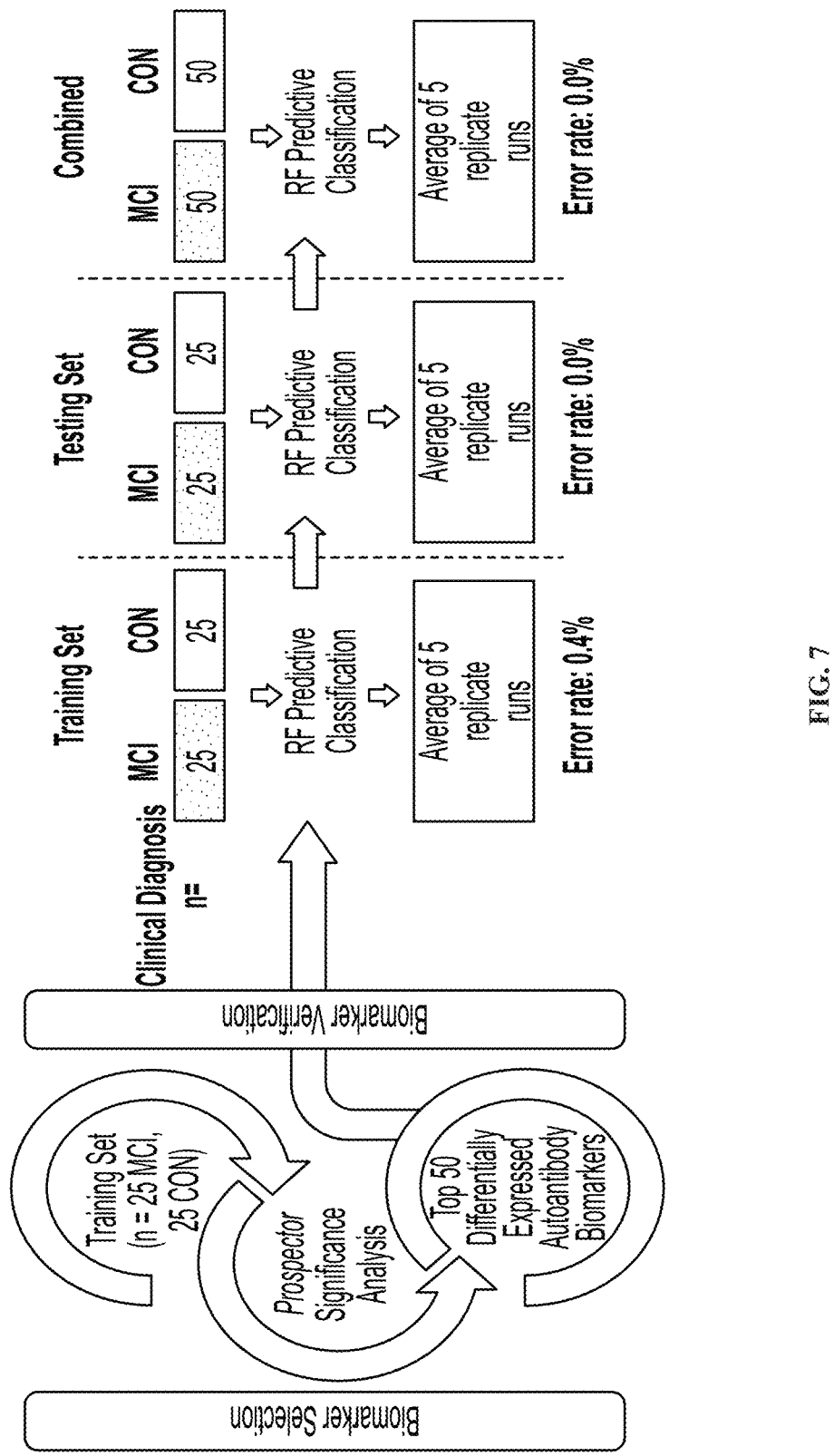
FIG. 7. represents the overall strategy for at least one exemplified embodiment of the present invention.

Example 1 demonstrates that a small panel of Early-Stage AD autoantibody biomarkers can be used to detect early-stage AD pathology in individuals with AD-driven MCI with very high overall accuracy. The overall strategy for Example 1 is found in FIG. 7. The subjects used were diagnosed as MCI by Alzheimer's Disease Neuroimaging (ADNI) investigators and were selected because they also exhibit low CSF A42 levels, a surrogate biochemical biomarker consistent with ongoing Early-Stage AD pathology that also serves as an indicator of likelihood of progression to Mid-Stage or Late-Stage AD. As used herein, MCI refers to "mild cognitive impairment," which as disclosed in this Application is a symptom of Early-Stage AD, thus MCI qualifies as Early-Stage AD Pathology.

Second, multiple and independent biomarker discovery strategies were found to yield autoantibody biomarker-target antigen panels that showed considerable overlap of selected autoantibody biomarkers and comparable diagnostic performance outcomes. Third, the selected panel of Early-Stage AD biomarkers and associated diagnostic logic was stage-specific in that it could differentiate these MCI subjects from individuals at a more advanced (mild-moderate) stage of AD. Lastly, the Early-Stage AD biomarkers described herein are also disease-specific in that they are capable of distinguishing subjects with MCI from those with Early- or Mild-Moderate-stage Parkinson's Disease (PD), Multiple Sclerosis (MS), and early-stage breast cancer.

Clinical, biochemical and imaging data used here were obtained from the ADNI database at UCLA. The ADNI was launched in 2003 by the National Institute on Aging, the National Institute of Biomedical Imaging and Bioengineering, the Food and Drug Administration, private pharmaceutical companies and non-profit organizations, as a $60 million, 5-year, public-private partnership. The primary goal of ADNI has been to test whether serial MRI, PET, and other biological markers, and clinical and neuropsychological assessments can be combined to measure the progression of Early-Stage AD. Determination of sensitive and specific markers of very early AD progression is intended to aid researchers and clinicians to develop new treatments and monitor their effectiveness, as well as to lessen the time and cost of clinical trials. The initial goal of ADNI was to recruit 800 adults, aged 55 to 90 years, to participate in the research approximately 200 cognitively normal older individuals to be followed for 3 years, and 200 people with early AD to be followed for 2 years.

Subjects were split into testing and training sets such that the training set included cases and controls matched by age and gender. The training set was used to rank candidate target antigens by their predictive power and to establish the diagnostic logic. The initial training set for Early-Stage AD consisted of 25 MCI (Early-Stage) samples and 25 control samples; with the remaining samples relegated to the independent testing set, thus also 25 MCI (Early-Stage) and 25 control subjects. The optimum number of target antigens was estimated, defined as the minimum number of target antigens required to maintain maximum diagnostic accuracy for this population of MCI (Early-Stage) subjects. This was accomplished by first comparing the predictive capacity of the top and bottom 25 target antigens, and then determining the efficacy of the top 10 alone using the original Training Set logic. In each case, the predictive classification accuracy of the target antigens in the Training Set, Testing Set, and in both sets combined was tested with R's Random Forest (RF) (v 4.6-10), using the default settings [19-21]. Selected target antigens were tested with the RF model algorithm, and classification accuracy is reported in a confusion matrix and misclassifications as an Out-Of-Bag (OOB) error score. Receiver operating characteristic curves (ROCs), widely used to evaluate the utility of a diagnostic test, were generated using R(3.02) packages ROCR(v 1.0-5) and pROC(v 1.7.3) [6,22]. Based on the determined optimal number of target antigens, a final model was constructed using these target antigens their associated Training Set logic and tested with the independent Testing Set.

Using the same Training and Testing Set strategy outlined above, we performed an additional round of biomarker discovery using only RF, instead of prevalence difference, to select potential biomarkers. Following M-statistical analysis by Prospector, the data was analyzed using the "variable importance" function in RF, which is the prediction accuracy of the OOB error score reported for each tree, and also for each individual permutated biomarker. The difference between the two values were averaged over all trees and normalized by the standard error. The top 50 biomarkers based on the normalized variable importance score were chosen as potential diagnostic biomarkers and further analyzed for their diagnostic value as reported below.

B. Participant Selection

The participants were comprised of fifty (50) ADNI individuals who were diagnosed with amnestic MCI at baseline and had at least one follow-up visit, thus qualifying criteria for Early-Stage AD. All subjects in the ADNI were 55-91 years of age and had no evidence of cerebrovascular disease (Modified Hachinski Ischemia Score less than or equal to 4 (21), no evidence of depression (Geriatric Depression Scale <6 (22), stable medications, a study partner, no visual or hearing impairment, good general health, 6 grades of education or equivalent, English or Spanish fluency, and no medical contraindications to MRI. This included baseline data from individuals diagnosed with MCI with available neuropsychological test results, APOE status, CSF proteins, 18F-fluorodeoxyglucose (FDG) PET, and structural MRI scans. In the ADNI samples, MCI was defined based on the following criteria: memory complaint verified by study partner; abnormal memory function based on education-adjusted cut-off on the Logical Memory II subscale from the Wechsler Memory Scale revised, MMSE score of 24-30 (inclusive), Clinical Dementia Rating score of 0.5, and cognitive and functional impairment not yet severe enough to meet criteria for AD or dementia.

Fifty MCI samples with confirmed low CSF Aβ42 from subjects participating in the ADNI2 study were obtained in coordination with the Alzheimer's Neuroimaging Disease Initiative. These came from subjects participating in the ADNI2 study, which was an ongoing longitudinal study with the goal of identifying individuals at risk for Alzheimer's disease, as well as the development of diagnostic and prognostic biomarkers of the disease. Diagnosis of MCI was made based on a battery of tests, including MMSE scores, CDR, and other subjective memory assessments. Fifty Mid-Stage AD serum samples were obtained from Analytical Biological Systems, Inc. (Wilmington, Del.). Healthy age- and sex-matched control sera were obtained from several sources: 27 from BioServe Biotechnologies Ltd.; 11 from Asterand Inc.; 9 from The New Jersey Institute for Successful Aging at Rowan University (Stratford, N.J.); and 3 from Analytical Biological Systems, Inc. All samples were handled using standard procedures and stored at −80° C. until use. Demographic characteristics of the study population are displayed in FIGS. 1A-1C.

C. Human Protein Microarrays

To identify Early-Stage AD autoantibody biomarkers in human sera, Invitrogen's ProtoArray v5.0 Human Protein Microarrays (Cat. No. PAH0525020, Invitrogen, Carlsbad, Calif., USA) was used, each containing 9,486 unique human protein antigens. All proteins were expressed as GST fusion proteins in insect cells, purified under native conditions, and spotted in duplicate onto nitrocellulose-coated glass slides. Arrays were probed with serum and scanned according to the manufacturer's instructions. Briefly, microarrays were blocked using Blocking Buffer (Cat. No. PA055, Invitrogen) and each was incubated with serum diluted to 1:500 in washing buffer. After washing, arrays were probed with anti-human IgG (H+L) conjugated to AlexaFluor 647 (Cat. No. A-21445, Invitrogen) diluted 1:2,000 in washing buffer. Arrays were then washed, dried, and immediately scanned with a GenePix 4000B Fluorescence Scanner (Molecular Devices, Sunnyvale, Calif., USA).

Fluorescence data was acquired by aligning the Genepix Array List (GAL) onto the microarray using the Genepix Pro analysis software. The resulting Genepix Results (GPR) files were imported into Invitrogen's Prospector 5.2 for analysis. The "group characterization" and "two-group comparison" features in the IRBP Toolbox within Prospector then enabled M-statistical analysis of differential autoantibody expression between the two groups (see Diagnostic Strategy, FIG. 7). Positive hits were determined by a Z-Factor greater than 0.4, and a minimum signal intensity of 1500 RFU, which allowed for stringent biomarker selection and minimizes the amount of false positives. Autoantibodies were sorted into descending order by difference of prevalence between early stage AD (MCI) and control groups, and the top 50 most differentially expressed autoantibodies were chosen as potential autoantibody biomarkers. All data is MIAME compliant and raw data from the microarrays have been deposited in a MIAME compliant database (GEO) under accession number GSE74763.

D. Selection of a Panel of Target Antigens Bound to Autoantibody Biomarkers for Early-Stage AD Diagnosis A panel of autoantibody biomarkers capable of specifically detecting Early-Stage AD pathology using 50 ADNI MCI patient sera, all with low CSF Aβ42 levels consistent with the presence of ongoing Early-Stage AD-related pathology as shown in FIG. 3 and each with a clinical diagnosis of either early MCI (EMCI, n=32) or late MCI (LMCI, n=18) was constructed according to criteria described herein. These sera, along with those obtained from age- and sex-matched controls, were used to probe commercially available human protein microarrays containing 9,486 proteins. First, samples were separated into Training and Testing Sets (FIG. 7), each containing 25 ADNI MCI sera (16 EMCI+9 LMCI) and 25 matched controls. The resulting individual autoantibody profiles for Training Set MCI subjects were compared with those of controls using Prospector analysis software. 193 target antigens were identified as bound to the autoantibody biomarkers with a significantly ($p<0.05$) higher prevalence in the MCI group compared to controls in the Training Set as potential autoantibody biomarkers.

E. Verification of Panel of Target Antigens Bound to Autoantibody Biomarkers Via Training and Testing Set Analysis The top 50 target antigens chosen from the Training Set (Table 1) were re-verified as significant predictors for specific binding to autoantibody biomarkers using Random Forest (RF) (Breiman L (2001) *Random Forests. Machine Learning* 45: 5-32). Upon RF evaluation of the Training Set samples (n=50; 25 MCI, 25 controls) utilizing the 50 selected target antigens, MCI subjects were distinguished from age- and sex-matched controls with an average of 99.6% prediction accuracy based on five replicate runs. These 50 target antigens and the RF Training Set logic were used to classify MCI in Testing Set subjects, comprised of a completely independent group of samples that played no role in biomarker selection. RF was able to correctly classify 100% of MCI and controls among Testing Set subjects (n=50; 25 MCI, 25 controls). Combining both Training and Testing Set samples and using the Training Set logic, RF successfully distinguished MCI from controls with no error. See FIG. 7. The diagnostic utility of this panel of 50 target antigens was also evaluated using Receiver Operating Characteristic (ROC) curve analysis of Testing Set subjects (FIG. 5B). The ROC area under the curve (AUC) for this comparison was 1, indicating exceptional classification accuracy. See FIG. 4. Diagnostic sensitivity, specificity and positive- and negative-predictive values for the 50 target antigens used to evaluate the Testing Set subjects are shown in FIGS. 2A-D.

F. Swapping Training and Testing Sets Yielded Similar Target Antigen Panels of Comparable Accuracy As a further test of the utility of autoantibodies as biomarkers for detecting Early-Stage AD pathology in MCI patients, a second round of biomarker discovery was carried out in which the Training and Testing sets were swapped and the resulting autoantibody-target antigen interactions were compared with those chosen in the first round. Using the panel of 50 newly selected target antigens, RF was able to correctly classify 98% of MCI and controls using Testing Set subjects (sensitivity=96.0%; specificity=100.0%; PPV=100.0%; NPV=96.2%; ROC AUC=1). Importantly, 26 of 50 (52%) newly selected target antigens in Table 2 below overlapped with those chosen in the first round.

TABLE 2

Target Antigen Overlap after Swapping Training and Testing Sets

| GenBank ID or Accession No. ID | Target Antigen |
| --- | --- |
| BC022098.1 | cDNA clone MGC: 31944 IMAGE: 4878869 |
| BC020233.1 | cDNA clone MGC: 31936 IMAGE: 4765518 |
| BC015833.1 | cDNA clone MGC: 27152 IMAGE: 4691630 |
| BC051762.1 | Uncharacterized protein C20orf96 |
| NM_016207.2 | cleavage and polyadenylation specific factor 3, 73 kDa (CPSF3) |
| BC030984.1 | cDNA clone MGC: 32654 IMAGE: 4701898 |
| NM_032855.1 | hematopoietic SH2 domain containing (HSH2D) |
| BC016380.1 | cDNA clone MGC: 27376 IMAGE: 4688477 |
| BC012104.1 | purinergic receptor P2Y, G-protein coupled, 2 (P2RY2) |
| BC053664.1 | zinc finger, FYVE domain containing 28 (ZFYVE28) |
| NM_000159.2 | glutaryl-Coenzyme A dehydrogenase (GCDH), nuclear gene encoding mitochondrial protein, transcript variant 1 |
| BC000468.1 | ubiquitin-conjugating enzyme E2 variant 1 (UBE2V1) |
| BC030813.1 | cDNA clone MGC: 22645 IMAGE: 4700961 |
| PHC1244 | chemokine (C-C motif) ligand 19 (CCL19) |
| BC032852.2 | melanoma antigen family B, 4 (MAGEB4) |
| BC104469.1 | Outer dense fiber protein 3-like protein 2 |
| NM_006374.2 | serine/threonine kinase 25 (STE20 homolog, yeast) (STK25) |
| NM_024692.3 | CAP-GLY domain containing linker protein family, member 4 (CLIP4) |
| NM_001098.2 | aconitase 2, mitochondrial (ACO2), nuclear gene encoding mitochondrial protein |
| PHG0046 | platelet-derived growth factor beta polypeptide (simian sarcoma viral (v-sis) oncogene homolog) (PDGFB), transcript variant 1 |
| XM_373800.2 | PREDICTED: *Homo sapiens* hypothetical LOC388528 (LOC388528) |
| BC056918.1 | glutathione S-transferase omega 2 (GSTO2) |
| BC017959.1 | chromosome 2 open reading frame 47 (C2orf47) |
| NM_018282.1 | Paraspeckle component 1 |
| NM_172160.1 | potassium voltage-gated channel, shaker-related subfamily, beta member 1 (KCNAB1), transcript variant 1 |
| BC007852.1 | Serine/threonine-protein kinase 25 |

G. Comparison of Target Antigen Selection Strategies: RF Vs Prevalence Difference A completely different and unbiased selection process using RF only was carried out instead of first ranking potential target antigens based on prevalence differences, data from Prospector was directly loaded into R and RF independently chose the target antigens as described in the Methods. Using the panel of 50 RF-selected target antigens (shown in Table 3 below), RF was able to correctly classify MCI and controls in Testing Set subjects with an average of 100% overall accuracy in five replicate runs, thus comparable to both panels derived from prevalence difference described above.

TABLE 3

RF-Selected Target Antigens

| GenBank ID or Accession No. ID | Target Antigen |
|---|---|
| NM_004582.2 | Rab geranylgeranyltransferase, beta subunit (RABGGTB) |
| BC020233.1 | cDNA clone MGC: 31936 IMAGE: 4765518, complete cds |
| BC015833.1 | cDNA clone MGC: 27152 IMAGE: 4691630, complete cds |
| NM_181791.1 | Probable G-protein coupled receptor 141 |
| BC056918.1 | glutathione S-transferase omega 2 (GSTO2) |
| BC022098.1 | cDNA clone MGC: 31944 IMAGE: 4878869, complete cds |
| NM_032855.1 | hematopoietic SH2 domain containing (HSH2D) |
| NM_002550.1 | Olfactory receptor 3A1 |
| NM_016207.2 | cleavage and polyadenylation specific factor 3, 73 kDa (CPSF3) |
| BC030984.1 | cDNA clone MGC: 32654 IMAGE: 4701898, complete cds |
| NM_022491.2 | Sin3 histone deacetylase corepressor complex component SDS3 |
| BC051762.1 | Uncharacterized protein C20orf96 |
| NM_000159.2 | glutaryl-Coenzyme A dehydrogenase (GCDH), nuclear gene encoding mitochondrial protein, transcript variant 1 |
| PHC1705 | fms-related tyrosine kinase 3 ligand (FLT3LG) |
| BC012104.1 | purinergic receptor P2Y, G-protein coupled, 2 (P2RY2) |
| BC016380.1 | cDNA clone MGC: 27376 IMAGE: 4688477, complete cds |
| NM_177437.1 | Taste receptor type 2 member 60 |
| NM_014926.2 | SLIT and NTRK-like protein 3 |
| 18S + 28S Ribosomal RNA | NA |
| NM_006428.3 | mitochondrial ribosomal protein L28 (MRPL28), nuclear gene encoding mitochondrial protein |
| BC067819.1 | transmembrane protein 29 (TMEM29) |
| BC053664.1 | zinc finger, FYVE domain containing 28 (ZFYVE28) |
| PHC0205 | interleukin 20 (IL20) |
| PHC1244 | chemokine (C-C motif) ligand 19 (CCL19) |
| NM_004987.3 | LIM and senescent cell antigen-like-containing domain protein 1 |
| BC015628.1 | 4-aminobutyrate aminotransferase (ABAT) |
| NM_007115.2 | tumor necrosis factor, alpha-induced protein 6 (TNFAIP6) |
| NM_182536.2 | gastrokine 2 (GKN2) |
| BC006206.2 | NIK and IKK{beta} binding protein (NIBP) |
| BC031053.1 | lecithin retinol acyltransferase (phosphatidylcholine-retinol O-acyltransferase) (LRAT) |
| NM_001098.2 | aconitase 2, mitochondrial (ACO2), nuclear gene encoding mitochondrial protein |
| NM_004669.2 | chloride intracellular channel 3 (CLIC3) |
| NM_014431.1 | Paladin |
| NM_032861.2 | serine active site containing 1 (SERAC1) |
| BC062613.1 | sodium channel, nonvoltage-gated 1 alpha (SCNN1A) |
| NM_007255.1 | xylosylprotein beta 1,4-galactosyltransferase, polypeptide 7 (galactosyltransferase I) (B4GALT7) |
| BC009464.1 | Alpha-1,3-mannosyl-glycoprotein 4-beta-N-acetylglucosaminyltransferase B |
| NM_020633.2 | Vomeronasal type-1 receptor 1 |
| NM_001290.1 | LIM domain binding 2 (LDB2) |
| BC000468.1 | ubiquitin-conjugating enzyme E2 variant 1 (UBE2V1) |
| BC029796.1 | hypothetical protein BC014011 (LOC116349) |
| BC098334.1 | RAP1, GTP-GDP dissociation stimulator 1 (RAP1GDS1), transcript variant 5, mRNA. |
| NM_014321.2 | origin recognition complex, subunit 6 like (yeast) (ORC6L) |
| NM_004403.1 | deafness, autosomal dominant 5 (DFNA5) |
| BC010852.1 | Aflatoxin B1 aldehyde reductase member 2 |
| NM_175614.2 | NADH dehydrogenase (ubiquinone) 1 alpha subcomplex, 11, 14.7 kDa (NDUFA11) |
| NM_005898.4 | cell cycle associated protein 1 (CAPRIN1), transcript variant 1 |
| PHC3016 | tumor necrosis factor (TNF superfamily, member 2) (TNF); see catalog number for detailed information on wild-type or point mutant status |
| BC031052.1 | TNF receptor-associated factor 6 (TRAF6) |
| PHG0046 | platelet-derived growth factor beta polypeptide (simian sarcoma viral (v-sis) oncogene homolog) (PDGFB), transcript variant 1 |

Importantly, 19 of the RF-selected target antigens shown in Table 4 below overlapped with those in Table 1.

TABLE 4

RF-Selected Target Antigen Overlap with Table 1

| GenBank ID or Accession No. ID | Target Antigen |
|---|---|
| BC022098.1 | cDNA clone MGC: 31944 IMAGE: 4878869, complete cds |
| BC020233.1 | cDNA clone MGC: 31936 IMAGE: 4765518, complete cds |
| BC015833.1 | cDNA clone MGC: 27152 IMAGE: 4691630, complete cds |
| NM_032855.1 | hematopoietic SH2 domain containing (HSH2D) |
| BC030984.1 | cDNA clone MGC: 32654 IMAGE: 4701898, complete cds |
| NM_016207.2 | cleavage and polyadenylation specific factor 3, 73 kDa (CPSF3) |
| BC016380.1 | cDNA clone MGC: 27376 IMAGE: 4688477, complete cds |
| BC051762.1 | Uncharacterized protein C20orf96 |
| PHC1244 | chemokine (C-C motif) ligand 19 (CCL19) |
| BC053664.1 | zinc finger, FYVE domain containing 28 (ZFYVE28) |
| BC012104.1 | purinergic receptor P2Y, G-protein coupled, 2 (P2RY2) |
| BC029796.1 | hypothetical protein BC014011 (LOC116349) |
| NM_000159.2 | glutaryl-Coenzyme A dehydrogenase (GCDH), nuclear gene encoding mitochondrial protein, transcript variant 1 |
| NM_001098.2 | aconitase 2, mitochondrial (ACO2), nuclear gene encoding mitochondrial protein |
| NM_007255.1 | xylosylprotein beta 1,4-galactosyltransferase, polypeptide 7 (galactosyltransferase I) (B4GALT7) |
| BC000468.1 | ubiquitin-conjugating enzyme E2 variant 1 (UBE2V1) |

TABLE 4-continued

RF-Selected Target Antigen Overlap with Table 1

| GenBank ID or Accession No. ID | Target Antigen |
|---|---|
| BC056918.1 | glutathione S-transferase omega 2 (GSTO2) |
| 18S + 28S Ribosomal RNA | NA |
| PHG0046 | platelet-derived growth factor beta polypeptide (simian sarcoma viral (v-sis) oncogene homolog) (PDGFB), transcript variant 1 |

H. Fewer than 50 Autoantibody Biomarker-Target Antigen Interactions is Sufficient for Accurate Detection of Early-Stage AD The top 50 target antigens from Table 1 sorted according to decreasing prevalence difference are shown below in Table 5.

TABLE 5

Top 50 Target Antigens

| GenBank ID or Accession No. | Target Antigen |
|---|---|
| BC022098.1 | cDNA clone MGC: 31944 IMAGE: 4878869 |
| BC020233.1 | cDNA clone MGC: 31936 IMAGE: 4765518 |
| BC015833.1 | cDNA clone MGC: 27152 IMAGE: 4691630 |
| NM_032855.1 | hematopoietic SH2 domain containing (HSH2D) |
| BC030984.1 | cDNA clone MGC: 32654 IMAGE: 4701898 |
| NM_016207.2 | cleavage and polyadenylation specific factor 3, 73 kDa (CPSF3) |
| BC016380.1 | cDNA clone MGC: 27376 IMAGE: 4688477 |
| BC051762.1 | Uncharacterized protein C20orf96 |
| PHC1346 | Recombinant Human Stromal Cell derived Factor-1a (SDF-1a) |
| XM_373800.2 | PREDICTED: *Homo sapiens* hypothetical LOC388528 (LOC388528) |
| PHC1244 | chemokine (C-C motif) ligand 19 (CCL19) |
| BC053664.1 | zinc finger, FYVE domain containing 28 (ZFYVE28) |
| BC012104.1 | purinergic receptor P2Y, G-protein coupled, 2 (P2RY2) |
| BC029796.1 | hypothetical protein BC014011 (LOC116349) |
| NM_000159.2 | glutaryl-Coenzyme A dehydrogenase (GCDH), nuclear gene encoding mitochondrial protein, transcript variant 1 |
| NM_001098.2 | aconitase 2, mitochondrial (ACO2), nuclear gene encoding mitochondrial protein |
| NM_014763.2 | mitochondrial ribosomal protein L19 (MRPL19), nuclear gene encoding mitochondrial protein |
| NM_018282.1 | Paraspeckle component 1 |
| XM_086879.4 | PREDICTED: *Homo sapiens* hypothetical LOC150371 (LOC150371) |
| BC104469.1 | Outer dense fiber protein 3-like protein 2 |
| BC032852.2 | melanoma antigen family B, 4 (MAGEB4) |
| NM_007255.1 | xylosylprotein beta 1,4-galactosyltransferase, polypeptide 7 (galactosyltransferase I) (B4GALT7) |
| NM_015891.2 | cell division cycle 40 homolog (S. cerevisiae) (CDC40) |
| NM_080548.1 | Tyrosine-protein phosphatase non-receptor type 6 |
| NM_006374.2 | serine/threonine kinase 25 (STE20 homolog, yeast) (STK25) |
| BC000468.1 | ubiquitin-conjugating enzyme E2 variant 1 (UBE2V1) |
| NM_182612.1 | Parkinson disease 7 domain containing 1 (PDDC1) |
| NM_001381.2 | docking protein 1, 62 kDa (downstream of tyrosine kinase 1) (DOK1) |
| thyroglobulin | NA |
| BC001304.1 | piccolo (presynaptic cytomatrix protein) (PCLO) |
| NM_017966.1 | vacuolar protein sorting 37 homolog C (S. cerevisiae) (VPS37C) |
| NM_003384.1 | vaccinia related kinase 1 (VRK1) |
| BC031068.1 | aminoadipate aminotransferase (AADAT) |
| BC030711.2 | Aprataxin and PNK-like factor |
| NM_024692.3 | CAP-GLY domain containing linker protein family, member 4 (CLIP4) |
| BC012423.1 | superoxide dismutase 2, mitochondrial (SOD2) |
| BC007852.1 | Serine/threonine-protein kinase 25 |
| NM_033377.1 | chorionic gonadotropin, beta polypeptide 1 [Source: RefSeq peptide; Acc: NP_203695] |
| NM_017451.1 | BAI1-associated protein 2 (BAIAP2), transcript variant 2 |
| BC056918.1 | glutathione S-transferase omega 2 (GSTO2) |
| 18S + 28S Ribosomal RNA | NA |
| NM_018357.2 | La ribonucleoprotein domain family, member 6 (LARP6), transcript variant 1 |
| NM_004732.1 | potassium voltage-gated channel, shaker-related subfamily, beta member 3 (KCNAB3) |
| PHG0046 | platelet-derived growth factor beta polypeptide (simian sarcoma viral (v-sis) oncogene homolog) (PDGFB), transcript variant 1 |
| BC030813.1 | cDNA clone MGC: 22645 IMAGE: 4700961 |
| NM_018039.2 | jumonji domain containing 2D (JMJD2D) |
| NM_022839.2 | mitochondrial ribosomal protein S11 (MRPS11), nuclear gene encoding mitochondrial protein, transcript variant 1 |
| NM_172160.1 | potassium voltage-gated channel, shaker-related subfamily, beta member 1 (KCNAB1), transcript variant 1 |
| BC017202.2 | Isovaleryl-CoA dehydrogenase, mitochondrial |
| BC017959.1 | chromosome 2 open reading frame 47 (C2orf47) |

The relative diagnostic accuracy of the top and bottom 25 autoantibody biomarker-target antigen interactions were compared within the selected panel for detecting MCI in Testing Set subjects. Results showed an overall accuracy of 100% for the top 25 autoantibody biomarker-target antigen interactions (sensitivity=100.0%; specificity=100.0%; ROC AUC=1) and 98.0% for the bottom 25 autoantibody biomarker-target antigen interactions (sensitivity=100.0%; specificity=96.0%; ROC AUC=1) for distinguishing MCI subjects from corresponding age-matched controls. See FIGS. 2A-C and 4. Next, the top 10 target autoantibody biomarker-target antigen interactions were tested independently and showed an overall accuracy of 98.0% (sensitivity=96.0%; specificity=100.0%; ROC AUC=1), suggesting that this small panel of target antigens is sufficient to achieve maximal overall accuracy. See FIGS. 2A and 4.

I. Disease Specificity of the Selected Autoantibody Biomarker-Target Antigen Interactions for AD The disease specificity for Early-Stage AD of the top 10 and top 50 autoantibody biomarker-target antigen interactions was evaluated to determine whether or not said autoantibody biomarker-target antigen interactions can successfully differentiate ADNI MCI subjects from those with other neurological and non-neurological diseases such as, but not necessarily, PD. To eliminate the possibility that the autoantibody biomarkers were simply detecting non-specific CNS degeneration, the same 25 MCI serum samples from Testing Set subjects were compared to sera obtained from 25 subjects with early-stage PD, 25 subjects with mild-moderate PD, 25 subjects with multiple sclerosis (MS) and 11 subjects with stage 0-2 breast cancer. Using the panel of 50 target antigens in Table 5, MCI sera were readily distinguished from early-stage PD sera with an overall accuracy of 98.0% (sensitivity=100.0%; specificity=96.0%; ROC AUC=1) and 96.0% for mild-moderate PD (sensitivity=96.0%; specificity=96.0%; ROC AUC=1) (FIG. 2A). Similarly, this panel was able to readily distinguish ADNI MCI subjects from MS and stage 0-2 breast cancer subjects with comparable overall accuracy. Comparable results were obtained using only the top 10 target antigens. See FIG. 2D.

Figure 6:
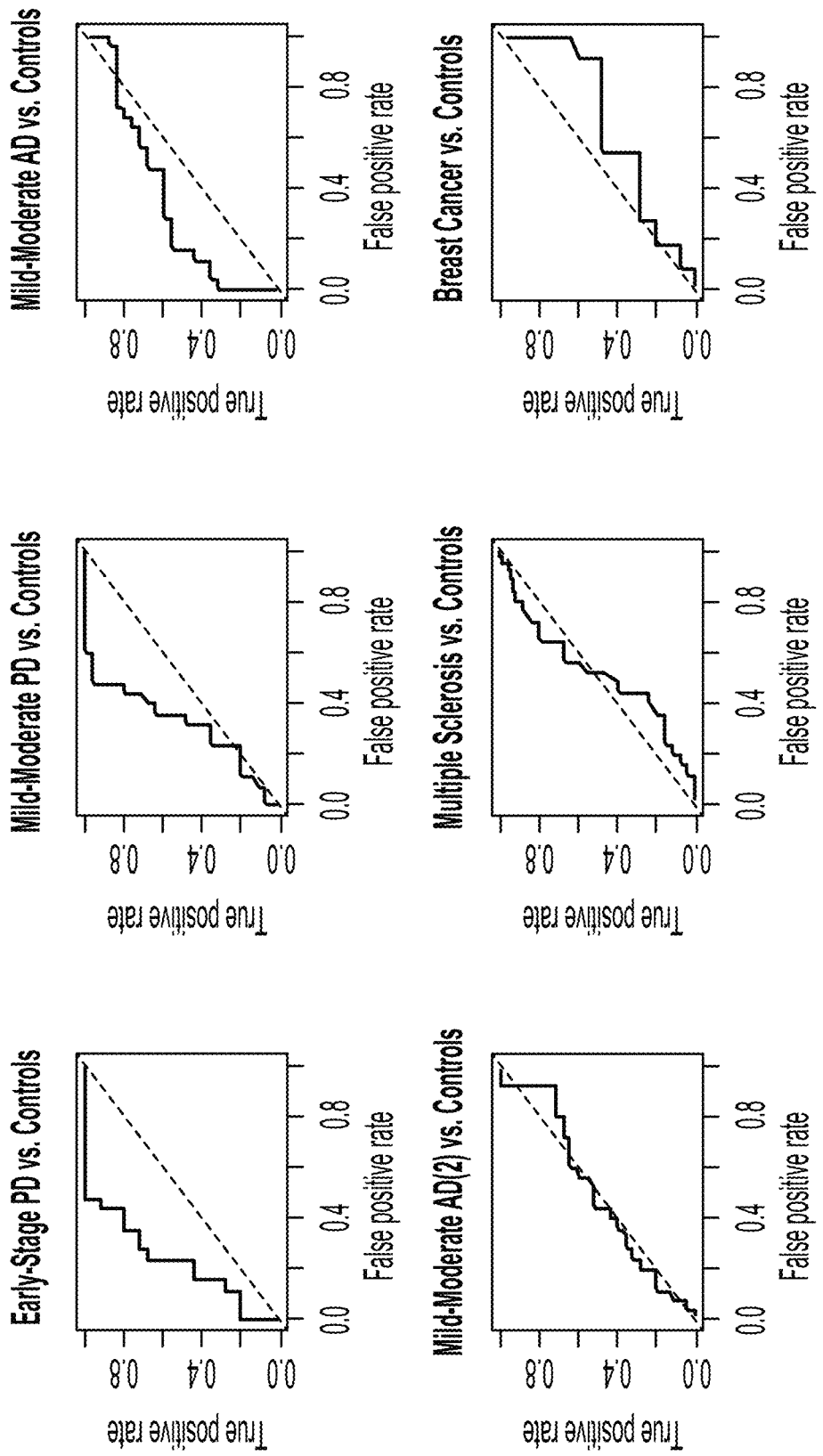
FIG. 6. represents the Target Antigen panel for Early-Stage AD.

A comparison of several neurodegenerative controls including Early-Stage PD, Mild-Moderate PD, Early-Stage AD, Multiple Sclerosis, and one non-neurodegenerative control, breast cancer, to normal control samples using the selected panel of 50 Target Antigens (shown in Table 5) to assess the specificity of the panel for Early-Stage AD is shown in FIG. 6. Using the panel of the top 50 MCI autoantibody biomarker-target antigen interactions, Random Forest was unable to successfully differentiate any of the disease groups from the control group, visualized by ROC curve analysis in FIG. 6. These results clearly demonstrate the specificity of the top 50 autoantibody biomarker-target antigen interactions, ruling out the possibility that they are nonspecific for CNS neurodegeneration, or disease in general.

J. Staging of AD: Autoantibody Biomarkers Can Distinguish Early Stage AD (MCI) Subjects from Those with Mid-Stage AD The autoantibody biomarkers of the present invention can be used to distinguish different stages of AD. To address this, the panel of 50 target antigens in Table 5 was used and the RF logic derived from the Training Set to test whether 25 ADNI Testing Set MCI samples could be distinguished from 50 subjects with Mid-Stage AD. The latter were split into two groups of 25 each and compared to the same Testing Set of 25 MCI samples, and the average overall accuracy from of both runs was 98.7%. See FIG. 2A. ROC curve analyses of all of these comparisons are presented in FIG. 5B. Taken together, these results confirm that, although AD-driven MCI, characteristic of Early-Stage AD, and Mid-Stage AD are different stages of the same disease and are expected to share autoantibody biomarkers, the target antigens shown in Table 5 for Early-Stage AD were capable of differentiating Early-Stage AD from more pathologically advanced stages of AD.

In addition to the 50 Early-Stage target antigens listed in Table 5, it was determined that autoantibody biomarker-target antigen interactions specific to Mid-Stage AD could also distinguish between these two discreet stages of the disease. 50 Mid-Stage AD samples were compared to the previously mentioned group of 50 control samples used for the MCI/Early-Stage AD samples, employing the same Training/Testing Set strategy as before. The top 50 most differentially expressed target antigens in Mid-Stage AD were selected and verified as significant using the same method described previously. Using this set of 50 target antigens, Early-Stage AD was readily distinguished from Mid-Stage AD with an overall accuracy, sensitivity, and specificity of 100.0% (data not shown). Comparison of the top 50 autoantibody biomarker-target antigen interactions for Early-Stage AD and those for Mild-Moderate AD revealed an overlap of 5 biomarker-target antigen interactions, or 10% of the total interactions, confirming the expected presence of common autoantibody biomarkers/target antigens between these disease stages, yet distinct enough to differentiate between the two.

Equivalents

One of ordinary skill in the art will recognize that there are many equivalents of the specific embodiments disclosed herein, and that those equivalents will require no more than routine experimentation in the art. Therefore, those equivalents must be considered part of this invention and as such must be considered to be covered by the following claims.

All references and citations disclosed herein are to be considered incorporated by reference in their entirety.

What is claimed is:

1. A method of detecting early-stage Alzheimer's Disease diagnostic autoantibodies in a subject in need thereof, the method comprising:
   (a) contacting an immunoglobulin-containing biological sample from the subject with an antigen set comprising antigens BC022098.1, NM_032855.1, and BC020233.1; under conditions under which each antigen from the antigen set forms an immunocomplex with the corresponding autoantibody if present in the biological sample,
   wherein each one of the antigens in the antigen set is attached to a substrate comprising a plurality of beads, each bead attached to one type of antigen;
   (b) binding the corresponding immunocomplexes with a detectable label such that the corresponding immunocomplexes are labeled; and
   (c) detecting the amount of the labeled corresponding immunocomplexes by measuring the detectable label.

2. The method of claim 1, wherein the subject is a human.

3. The method of claim 1, wherein the biological sample is selected from the group consisting of whole blood, serum, cerebrospinal fluid, saliva, and sputum.

4. The method of claim 1, wherein the plurality of beads are magnetic or non-magnetic beads.

5. The method of claim 1, wherein the antigen set further comprises antigen, NM_004987.3.

6. A kit for detecting early-stage Alzheimer's Disease (ESAD) diagnostic biomarkers comprising:
   (a) an antigen set comprising at least two antigens selected from the group consisting of: BC022098.1, NM_032855.1, and BC020233.1,
   wherein each one of the antigens in the antigen set is attached to a substrate comprising a plurality of beads, each bead attached to one type of antigen; and
   (b) assay reagents for detection of the amount of the immunocomplexes formed by binding of the at least two antigens in the antigen set to their corresponding ESAD diagnostic biomarkers in an immunoglobulin-containing biological sample from a subject,
   wherein the assay reagents comprise a detectable label for labeling the formed immunocomplexes.

7. The kit of claim 6, wherein the antigen set further comprises antigen BC056918.1.

8. The kit of claim 6, wherein the antigen set further comprises antigen NM_004987.3.

9. The kit of claim 6, wherein the at least two antigens are BC022098.1 and BC020233.1.

10. The kit of claim 6, wherein the plurality of beads are magnetic or non-magnetic beads.

11. The kit of claim 10, wherein the plurality of beads are polymer or glass beads.

12. The method of claim 4, wherein the plurality of beads are polymer or glass beads.

13. The kit of claim 6, wherein the at least two antigens are BC022098.1, NM_032855.1 and BC020233.1, and the antigen set further comprises NM_004987.3.

14. The kit of claim 13, wherein the antigen set further comprises antigen BC056918.1.

* * * * *

SEQUENCE LISTING

```
<160> NUMBER OF SEQ ID NOS: 10

<210> SEQ ID NO 1
<211> LENGTH: 919
<212> TYPE: DNA
<213> ORGANISM: Homo sapiens

<400> SEQUENCE: 1
cacaagaggc agcactcagg acaatctcca gcatggcctg gtctcctctc ctcctcactc      60
tcctcgctca ctgcacaggg tcctgggccc agtctgtgct gacgcagccg ccctcagtgt     120
ctggggcccc agggcagagg gtcaccatct cctgcactgg gagcagttcc aacatcgggg     180
caggttatga tgtacactgg taccagcagc ttccaggaac agcccccaaa ctcctcatct     240
atggtaacag caatcggccc tcagggggtcc ctgaccgatt ctctggctcc aagtctggca     300
```

-continued

| | |
|---|---|
| cctcagcctc cctggccatc actgggctcc aggctgagga tgaggctgat tattactgcc | 360 |
| aatcctatga ctacagcctg agtgcttcgg gggtgttcgg cggagggacc aagctgaccg | 420 |
| tcctaggtca gcccaaggct gccccctcgg tcactctgtt cccgccctcc tctgaggagc | 480 |
| ttcaagccaa caaggccaca ctggtgtgtc tcataagtga cttctacccg ggagccgtga | 540 |
| cagtggcctg aaggcagat agcagccccg tcaaggcggg agtggagacc accacaccct | 600 |
| ccaaacaaag caacaacaag tacgcggcca gcagctacct gagcctgacg cctgagcagt | 660 |
| ggaagtccca cagaagctac agctgccagg tcacgcatga agggagcacc gtggagaaga | 720 |
| cagtggcccc tacagaatgt tcataggttc taaaccctca ccccccccac gggagactag | 780 |
| agctgcagga tcccagggga ggggtctctc ctcccacccc aaggcatcaa gcccttctcc | 840 |
| ctgcactcaa taaaccctca ataaatattc tcattgtcaa tcaaaaaaaa aaaaaaaaa | 900 |
| aaaaaaaaaa aaaaaaaa | 919 |

<210> SEQ ID NO 2
<211> LENGTH: 237
<212> TYPE: PRT
<213> ORGANISM: Homo sapiens

<400> SEQUENCE: 2

```
Met Ala Trp Ser Pro Leu Leu Thr Leu Leu Ala His Cys Thr Gly
1               5                   10                  15

Ser Trp Ala Gln Ser Val Leu Thr Gln Pro Ser Val Ser Gly Ala
                20                  25                  30

Pro Gly Gln Arg Val Thr Ile Ser Cys Thr Gly Ser Ser Asn Ile
                35                  40                  45

Gly Ala Gly Tyr Asp Val His Trp Tyr Gln Gln Leu Pro Gly Thr Ala
            50                  55                  60

Pro Lys Leu Leu Ile Tyr Gly Asn Ser Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Thr Gly Leu Gln Ala Glu Asp Glu Ala Asp Tyr Tyr Cys Gln Ser Tyr
                100                 105                 110

Asp Tyr Ser Leu Ser Ala Ser Gly Val Phe Gly Gly Thr Lys Leu
            115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
                180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235
```

<210> SEQ ID NO 3
<211> LENGTH: 903
<212> TYPE: DNA

<213> ORGANISM: Homo sapiens

<400> SEQUENCE: 3

```
ggcataagag gcagcactca ggacaatctc cagcatggcc tggtctcctc tcctcctcac      60
tctcctcgct cactgcacag ggtcctgggc ccagtctgtg ctgacgcagc cgccctcagt     120
gtctggggcc ccagggcaga gggtcaccat ctcctgcact gggagcagct ccaacatcgg     180
ggcaggttat gatgtacact ggtaccagca gcttccagga acagccccca aactcctcat     240
ctatggtaac agcaatcggc cctcaggggt ccctgaccga ttctctggct ccaagtctgg     300
cacctcagcc tccctggcca tcactgggct ccaggctgag gatgaggctg attattactg     360
ccagtcctat gacagcagcc tgagtggttt tgtggtattc ggcggaggga ccaagctgac     420
cgtcctaggt cagcccaagg ctgccccctc ggtcactctg ttcccgccct cctctgagga     480
gcttcaagcc aacaaggcca cactggtgtg tctcataagt gacttctacc cgggagccgt     540
gacagtggcc tggaaggcag atagcagccc cgtcaaggcg ggagtggaga ccaccacacc     600
ctccaaacaa agcaacaaca gtacgcggc cagcagctat ctgagcctga cgcctgagca     660
gtggaagtcc cacagaagct acagctgcca ggtcacgcat gaagggagca ccgtggagaa     720
gacagtggcc cctacagaat gttcataggt tctcaaccct cacccccac cacgggagac     780
tagagctgca ggatcccagg ggaggggtct ctcctcccac cccaaggcat caagcccttc     840
tccctgcact caataaaccc tcaataaata ttctcattgt caatcaaaaa aaaaaaaaa     900
aaa                                                                    903
```

<210> SEQ ID NO 4
<211> LENGTH: 237
<212> TYPE: PRT
<213> ORGANISM: Homo sapiens

<400> SEQUENCE: 4

```
Met Ala Trp Ser Pro Leu Leu Leu Thr Leu Leu Ala His Cys Thr Gly
 1               5                  10                  15

Ser Trp Ala Gln Ser Val Leu Thr Gln Pro Pro Ser Val Ser Gly Ala
            20                  25                  30

Pro Gly Gln Arg Val Thr Ile Ser Cys Thr Gly Ser Ser Ser Asn Ile
        35                  40                  45

Gly Ala Gly Tyr Asp Val His Trp Tyr Gln Gln Leu Pro Gly Thr Ala
    50                  55                  60

Pro Lys Leu Leu Ile Tyr Gly Asn Ser Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Thr Gly Leu Gln Ala Glu Asp Glu Ala Asp Tyr Tyr Cys Gln Ser Tyr
            100                 105                 110

Asp Ser Ser Leu Ser Gly Phe Val Val Phe Gly Gly Gly Thr Lys Leu
        115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190
```

Ser Asn Asn Lys Tyr Ala Ala Ser Ser Tyr Leu Ser Leu Thr Pro Glu
    195                 200                 205

Gln Trp Lys Ser His Arg Ser Tyr Ser Cys Gln Val Thr His Glu Gly
210                 215                 220

Ser Thr Val Glu Lys Thr Val Ala Pro Thr Glu Cys Ser
225                 230                 235

<210> SEQ ID NO 5
<211> LENGTH: 2403
<212> TYPE: DNA
<213> ORGANISM: Homo sapiens

<400> SEQUENCE: 5

```
gtccttccca agaccacacc caggtccagt cattccctag gacttggcag agagctgtac      60
tcacagccaa gatcacagca aaatcagcaa agggaaaagg catgcagagt gaagtccaga     120
ggcaaccaga cagaagcatc cagaatcctc tcacagtggg gtcacacacc ccatgcttaa     180
ctcccccaac aatgagttgt aacaacagtc aggtgtggtg gtgtgtgcct gtagtcccag     240
ctacttggga gcctgaggca ggaggatcac ttgagtccag cagttcaaga ctgcagtgag     300
ctatgatcat accactgcac tccagcctga gtgacagagt gaaactctgt ctctaaaata     360
gggctcacct gcttgaggaa acaggaactg cctcggggca gccagccccg ccccattgac     420
gtgcagacct tgaatcgaaa cccaggctcc tgcaggcact gcacagcta cagcgagggc     480
ctcggccatc caagggtctc ccaggtgacc ttccctccac cccaggaagc tatgacagag     540
gccgggaagc tgcccctacc gctacccccca cggctggact ggtttgtgca cacccagatg     600
ggccagctgg cccaagacgg ggtccccgag tggttccatg gtgcaatctc aagagaggat     660
gctgagaact tgctggagtc acagccactg ggatcctttc tcatcagggt cagtcacagc     720
catgtgggct acacactctc ctacaaagcc caaagcagct gctgccattt catggtgaag     780
ctcttggatg atgggacttt catgatcccc ggggagaagg tggcccacac ctcgctggac     840
gccctggtca ccttccacca gcagaagcca attgagccgc gcagggagct gctgacacag     900
ccctgcaggc agaaggatcc cgcaaacgtg gattacgagg atctcttcct ctactccaac     960
gcagtggccg aggaagctgc ctgcccggtg tctgcccctg aggaggcctc cccaaagcca    1020
gtcctgtgtc accaatcaaa ggaaaggaag ccgtcagcag agatgaacag aataaccacc    1080
aaggaagcca cttcctcctg ccccccaaaa tcccctcttg agagacccg ccagaaactc    1140
tggaggagcc tcaaaatgct ccccgagaga ggccagaggg tccggcagca gctaaaaagc    1200
cacctcgcca ctgtgaactt gtcgtcactc ttggatgtcc ggagatccac ggtgatctca    1260
ggccctggga ccggaaaagg cagccaagat cactcagggg atcccaccte ggggacagga    1320
ggctacacgg atccctgtgt ggccacatct ctcaaaagcc cctcacagcc ccaggcacca    1380
aaagacagaa aggtccccac caggaaggcc gagaggtcgg tcagctgcat tgaggtgacc    1440
ccaggggaca ggagttggca ccaaatggta gtgagagccc tatcctccca ggagtccaag    1500
ccagagcacc agggcttggc agagcctgag aacgaccagc tcccggagga gtaccaacaa    1560
ccgccaccct tgcccctggg gtactgctag agaacaggtc cacctggct ctgggactcg    1620
ctgccagggg ctgccacact cctgaatgcc ttaacatttc ttccatggcc ccacaccatg    1680
gcatccgggg gtcttcggga acccgggaaa tggaataaag atgttttggg ggtctgttcc    1740
tgcactcacc catggggtga gctggttatt ttagcaacaa tcatcagagt gacgctgatg    1800
gtttggggca ccagctatac atcagcccca gtgccagacc ttctattcat tattttacgc    1860
```

```
ctcagagcaa ggccctcagg gagggtcatc ctccatgttt tgaagaagag actgaggttc    1920
agagaggata agaggcgtga ccaaggccac agagctatgg gtgtcagcac caggatttga    1980
agccaggtga atccgagccc ttttcccata tcatctgttt gttctgttgt ctaaaagcac    2040
actgcaagcc gggctcagtg gctcatgcct gtagtcccag cactctgtgg ggccgaggca    2100
ggcagatcgc ttgaggtcag gagttcgaga ccagcctggc caacatggtg aaaccccgtc    2160
tatactaaaa aattcaaaaa ttacccggac gtggtggcgc atgcctgtaa tcccagctac    2220
ttgggagcct gaggcgggag aattgcttga acccgggagg cagaggttgc agtgagccga    2280
gatcgcatca ctgcagtcca gcctggatga cagagtgaga ctccatctca aaaataaat    2340 aaataaataa aaatgaaatt aaaaaataaa aaaaaaaaaa aaaaaaaaaa aaaaaaaaa    2400 aaa                                                                 2403
```

<210> SEQ ID NO 6
<211> LENGTH: 352
<212> TYPE: PRT
<213> ORGANISM: Homo sapiens
<400> SEQUENCE: 6

```
Met Thr Glu Ala Gly Lys Leu Pro Leu Pro Leu Pro Pro Arg Leu Asp
1               5                   10                  15

Trp Phe Val His Thr Gln Met Gly Gln Leu Ala Gln Asp Gly Val Pro
            20                  25                  30

Glu Trp Phe His Gly Ala Ile Ser Arg Glu Asp Ala Glu Asn Leu Leu
        35                  40                  45

Glu Ser Gln Pro Leu Gly Ser Phe Leu Ile Arg Val Ser His Ser His
    50                  55                  60

Val Gly Tyr Thr Leu Ser Tyr Lys Ala Gln Ser Ser Cys Cys His Phe
65                  70                  75                  80

Met Val Lys Leu Leu Asp Asp Gly Thr Phe Met Ile Pro Gly Glu Lys
                85                  90                  95

Val Ala His Thr Ser Leu Asp Ala Leu Val Thr Phe His Gln Gln Lys
            100                 105                 110

Pro Ile Glu Pro Arg Arg Glu Leu Leu Thr Gln Pro Cys Arg Gln Lys
        115                 120                 125

Asp Pro Ala Asn Val Asp Tyr Glu Asp Leu Phe Leu Tyr Ser Asn Ala
    130                 135                 140

Val Ala Glu Glu Ala Ala Cys Pro Val Ser Ala Pro Glu Glu Ala Ser
145                 150                 155                 160

Pro Lys Pro Val Leu Cys His Gln Ser Lys Glu Arg Lys Pro Ser Ala
                165                 170                 175

Glu Met Asn Arg Ile Thr Thr Lys Glu Ala Thr Ser Ser Cys Pro Pro
            180                 185                 190

Lys Ser Pro Leu Gly Glu Thr Arg Gln Lys Leu Trp Arg Ser Leu Lys
        195                 200                 205

Met Leu Pro Glu Arg Gly Gln Arg Val Arg Gln Gln Leu Lys Ser His
    210                 215                 220

Leu Ala Thr Val Asn Leu Ser Ser Leu Leu Asp Val Arg Arg Ser Thr
225                 230                 235                 240

Val Ile Ser Gly Pro Gly Thr Gly Lys Gly Ser Gln Asp His Ser Gly
                245                 250                 255

Asp Pro Thr Ser Gly Asp Arg Gly Tyr Thr Asp Pro Cys Val Ala Thr
            260                 265                 270
```

```
Ser Leu Lys Ser Pro Ser Gln Pro Gln Ala Pro Lys Asp Arg Lys Val
        275                 280                 285

Pro Thr Arg Lys Ala Glu Arg Ser Val Ser Cys Ile Glu Val Thr Pro
    290                 295                 300

Gly Asp Arg Ser Trp His Gln Met Val Val Arg Ala Leu Ser Ser Gln
305                 310                 315                 320

Glu Ser Lys Pro Glu His Gln Gly Leu Ala Glu Pro Glu Asn Asp Gln
                325                 330                 335

Leu Pro Glu Glu Tyr Gln Gln Pro Pro Phe Ala Pro Gly Tyr Cys
            340                 345                 350
```

<210> SEQ ID NO 7
<211> LENGTH: 1546
<212> TYPE: DNA
<213> ORGANISM: Homo sapiens

<400> SEQUENCE: 7

| | | | | | |
|---|---|---|---|---|---|
| accacctctg | ctgccgcgcg | cctaccggag | ccgcttggcc | ctagtgcttt | ccagcggatt | 60 |
| tcccctcagg | tgcggagccg | ggtgccgggg | tcccacagcc | aaccactacc | ggttcctctt | 120 |
| tcgtcagcca | ccggcgccgg | caggacccgc | gaatcccgat | ctccaggagc | ctgtaaggag | 180 |
| gccgcccatt | ggctcagccg | cactgctggg | caggtacttc | caaagctttg | aggattggct | 240 |
| gatgctctgg | gcgccgggc | tagttggcgg | gtaggatcac | gtgcgagggg | caggccccgt | 300 |
| ctaggccccg | cctccttgct | gctgctgccg | ccgccaatcc | tggtccggtt | gcccgagttc | 360 |
| ccggaggtct | ctcgcgggac | ctctctcacc | gccaccgctc | ctactctcgg | gcttccaaat | 420 |
| ctggggcgat | gtctccccag | gttaaattac | cctagctcct | gctccagatc | gcttccccgt | 480 |
| gccccgccag | agcccagtag | ttcaaaaatt | aaatttgggg | caaggggtgc | gcgccagagc | 540 |
| gcagctgttt | ctggagcctg | cggcagcggt | ggcgagccac | agggcggcga | ccgtgagctc | 600 |
| cgggagctgc | gcaaaccacc | tggagaccat | gtctggggat | gcgaccagga | ccctggggaa | 660 |
| aggaagccag | cccccagggc | cagtcccgga | ggggctgatc | cgcatctaca | gcatgaggtt | 720 |
| ctgccectat | tctcacagga | cccgcctcgt | cctcaaggcc | aaagacatca | gacatgaagt | 780 |
| ggtcaacatt | aacctgagaa | acaagcctga | atggtactat | acaaagcacc | cttttggcca | 840 |
| cattcctgtc | ctggagacca | gccaatgtca | actgatctat | gaatctgtta | ttgcttgtga | 900 |
| gtacctggat | gatgcttatc | aggaaggaa | gctgtttcca | tatgacccct | tgaacgagc | 960 |
| tcgccaaaag | atgttattgg | agctattttg | taaggtccca | catttgacca | aggagtgcct | 1020 |
| ggtagcgttg | agatgtggga | gagaatgcac | taatctgaag | gcagccctgc | gtcaggaatt | 1080 |
| cagcaacctg | gaagagattc | ttgagtatca | gaacaccacc | ttctttggtg | gaacctgtat | 1140 |
| atccatgatt | gattacctcc | tctggccctg | gtttgagcgg | ctggatgtgt | atgggatact | 1200 |
| ggactgtgtg | agccacacgc | cagccctgcg | gctctggata | tcagccatga | agtgggaccc | 1260 |
| cacagtctgt | gctcttctca | tggataagag | cattttccag | ggcttcttga | atctctattt | 1320 |
| tcagaacaac | cctaatgcct | ttgactttgg | gctgtgctga | gtctcactgt | ccaccccttc | 1380 |
| gctgtccaga | attccccagc | ttgttgggag | tctacgtcac | ggcttgtctt | gggaaccaat | 1440 |
| ccgtctctct | ttcttttctt | tgaagttccc | aataaaatga | aaacaggaaa | tgtaaaaaaa | 1500 |
| aaaaaaaaaa | aaaaaaaaaa | aaaaaaaaaa | aaaaaaaaa | aaaaaa | | 1546 |

<210> SEQ ID NO 8
<211> LENGTH: 243

<212> TYPE: PRT
<213> ORGANISM: Homo sapiens

<400> SEQUENCE: 8

```
Met Ser Gly Asp Ala Thr Arg Thr Leu Gly Lys Gly Ser Gln Pro Pro
1               5                   10                  15

Gly Pro Val Pro Glu Gly Leu Ile Arg Ile Tyr Ser Met Arg Phe Cys
            20                  25                  30

Pro Tyr Ser His Arg Thr Arg Leu Val Leu Lys Ala Lys Asp Ile Arg
        35                  40                  45

His Glu Val Val Asn Ile Asn Leu Arg Asn Lys Pro Glu Trp Tyr Tyr
    50                  55                  60

Thr Lys His Pro Phe Gly His Ile Pro Val Leu Glu Thr Ser Gln Cys
65                  70                  75                  80

Gln Leu Ile Tyr Glu Ser Val Ile Ala Cys Glu Tyr Leu Asp Asp Ala
                85                  90                  95

Tyr Pro Gly Arg Lys Leu Phe Pro Tyr Asp Pro Tyr Glu Arg Ala Arg
            100                 105                 110

Gln Lys Met Leu Leu Glu Leu Phe Cys Lys Val Pro His Leu Thr Lys
        115                 120                 125

Glu Cys Leu Val Ala Leu Arg Cys Gly Arg Glu Cys Thr Asn Leu Lys
    130                 135                 140

Ala Ala Leu Arg Gln Glu Phe Ser Asn Leu Glu Ile Leu Glu Tyr
145                 150                 155                 160

Gln Asn Thr Thr Phe Phe Gly Gly Thr Cys Ile Ser Met Ile Asp Tyr
                165                 170                 175

Leu Leu Trp Pro Trp Phe Glu Arg Leu Asp Val Tyr Gly Ile Leu Asp
            180                 185                 190

Cys Val Ser His Thr Pro Ala Leu Arg Leu Trp Ile Ser Ala Met Lys
        195                 200                 205

Trp Asp Pro Thr Val Cys Ala Leu Leu Met Asp Lys Ser Ile Phe Gln
    210                 215                 220

Gly Phe Leu Asn Leu Tyr Phe Gln Asn Asn Pro Asn Ala Phe Asp Phe
225                 230                 235                 240

Gly Leu Cys
```

<210> SEQ ID NO 9
<211> LENGTH: 915
<212> TYPE: DNA
<213> ORGANISM: Homo sapiens

<400> SEQUENCE: 9

```
gggggggtc acaagaggca gcgctctcgg gacgtctcca ccatggcctg ggctctgctg     60
ctcctcactc tcctcactca ggacacaggg tcctgggccc agtctgccct gactcagcct    120
gcctccgtgt ctgggtctcc tggacagtcg atcaccatct cctgcactgg aaccagcact    180
gatgttggga gtcatagcct tgtctcctgg taccaacagc acccaggcaa agcccccaaa    240
tttcttattt cgagggcag taagcggccc tcaggggttt cgaatcgctt ctctggctcc     300
aagtctggca acacggcctc cctgacaatc tctgggctcc aggctgagga cgaggctgat    360
tattactgct gttcatatgt tggtagtggc actgtggttt tcggcggagg gacgaagctg    420
accgtcctag gtcagcccaa ggctgccccc tcggtcactc tgttcccgcc ctcctctgag    480
gagcttcaag ccaacaaggc cacactggtg tgtctcataa gtgacttcta cccgggagcc    540
gtgacagtgg cctggaaggc agatagcagc cccgtcaagg cgggagtgga gaccaccaca    600
```

-continued

```
ccctccaaac aaagcaacaa caagtacgcg gccagcagct atctgagcct gacgcctgag      660
cagtggaagt cccacagaag ctacagctgc caggtcacgc atgaagggag caccgtggag      720
aagacagtgg cccctacaga atgttcatag gttctcaacc ctcaccccca ccacgggaga      780
ctagagctgc aggatcccag ggagggggtc tctcctccca ccccaaggca tcaagccctt      840
ctccctgcac tcaataaacc ctcaataaat attctcattg tcaagcaaaa aaaaaaaaa       900 aaaaaaaaaa aaaaa                                                       915
```

<210> SEQ ID NO 10
<211> LENGTH: 235
<212> TYPE: PRT
<213> ORGANISM: Homo sapiens

<400> SEQUENCE: 10

```
Met Ala Trp Ala Leu Leu Leu Thr Leu Leu Thr Gln Asp Thr Gly
 1                5                  10                  15

Ser Trp Ala Gln Ser Ala Leu Thr Gln Pro Ala Ser Val Ser Gly
                 20                  25                  30

Ser Pro Gly Gln Ser Ile Thr Ile Ser Cys Thr Gly Thr Ser Thr Asp Val
                 35                  40                  45

Gly Ser His Ser Leu Val Ser Trp Tyr Gln Gln His Pro Gly Lys Ala
                 50                  55                  60

Pro Lys Phe Leu Ile Phe Glu Gly Ser Lys Arg Pro Ser Gly Val Ser
 65                   70                  75                  80

Asn Arg Phe Ser Gly Ser Lys Ser Gly Asn Thr Ala Ser Leu Thr Ile
                 85                  90                  95

Ser Gly Leu Gln Ala Glu Asp Glu Ala Asp Tyr Tyr Cys Cys Ser Tyr
                100                 105                 110

Val Gly Ser Gly Thr Val Val Phe Gly Gly Thr Lys Leu Thr Val
                115                 120                 125

Leu Gly Gln Pro Lys Ala Ala Pro Ser Val Thr Leu Phe Pro Pro Ser
                130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
                180                 185                 190

Asn Lys Tyr Ala Ala Ser Ser Tyr Leu Ser Leu Thr Pro Glu Gln Trp
                195                 200                 205

Lys Ser His Arg Ser Tyr Ser Cys Gln Val Thr His Glu Gly Ser Thr
                210                 215                 220

Val Glu Lys Thr Val Ala Pro Thr Glu Cys Ser
225                 230                 235
```